United States Patent
Hirata et al.

(10) Patent No.: US 7,609,386 B2
(45) Date of Patent: Oct. 27, 2009

(54) OPTICAL CHARACTERISTIC MEASURING APPARATUS

(75) Inventors: Takaaki Hirata, Tokyo (JP); Minoru Maeda, Tokyo (JP)

(73) Assignee: Yokogawa Electric Corporation, Tokyo (JP)

( * ) Notice: Subject to any disclaimer, the term of this patent is extended or adjusted under 35 U.S.C. 154(b) by 0 days.

(21) Appl. No.: 12/277,032

(22) Filed: Nov. 24, 2008

(65) Prior Publication Data

US 2009/0079991 A1 Mar. 26, 2009

Related U.S. Application Data

(62) Division of application No. 11/443,344, filed on May 31, 2006, now Pat. No. 7,538,885.

(30) Foreign Application Priority Data

| May 31, 2005 | (JP) | ............... P.2005-159061 |
| Jun. 3, 2005 | (JP) | ............... P.2005-163825 |
| Jun. 10, 2005 | (JP) | ............... P.2005-171310 |

(51) Int. Cl.
*G01B 11/02* (2006.01)

(52) U.S. Cl. .................. 356/492; 356/485
(58) Field of Classification Search ......... 356/484–487, 356/491–493
See application file for complete search history.

(56) References Cited

U.S. PATENT DOCUMENTS

| 6,376,830 B1 | 4/2002 | Froggatt et al. |
| 6,590,666 B2 * | 7/2003 | Baney et al. ............... 356/484 |
| 7,538,885 B2 * | 5/2009 | Hirata et al. ............... 356/485 |

FOREIGN PATENT DOCUMENTS

| JP | 2002-243585 A | 8/2002 |
| JP | 2004-20567 A | 1/2004 |

OTHER PUBLICATIONS

Connie J. Chang-Hasnain; "Tunable VCSEL";, IEEE Journal on Selected Topics in Quantum Electronics, vol. 6, No. 6, Nov./Dec. 2000; pp. 978-987.
D. Vakhshoori, et al.; "MEMs-Tunable Vertical-Cavity surface-Emitting Lasers"; Nortel Networks.

* cited by examiner

*Primary Examiner*—Patrick J Connolly
(74) *Attorney, Agent, or Firm*—Sughrue Mion, PLLC

(57) ABSTRACT

An optical characteristic measuring apparatus includes: a light source section which sweeps wavelengths of a first input light and a second input light respectively, frequencies of the first and second input lights being different from each other and polarized states of the first and second input lights being perpendicular to each other, and outputs the first and second input light; an interference section which inputs one branched light of the first and second input lights to a measuring object, makes output light from the measuring object interfere with other branched light of the first and second input lights, and outputs a plurality of interference lights; a plurality of light receiving sections which are respectively provided for the interference lights, receives the interference lights respectively, and outputs signals in accordance with optical powers of the interference lights respectively; and a low-pass filter for filtering the outputted signals.

8 Claims, 17 Drawing Sheets

OPTICAL CHARACTERISTIC MEASURING APPARATUS

This is a divisional of application Ser. No. 11/443,344 filed May 31, 2006 now U.S. Pat. No. 7,538,885. The entire disclosure(s) of the prior application(s), application number(s) Ser. No. 11/443,344 is considered part of the disclosure of the accompanying divisional application and is hereby incorporated by reference.

This application claims foreign priorities based on Japanese Patent application No. 2005-159061, filed May 31, 2005, Japanese Patent application No. 2005-163825, filed Jun. 3, 2005, and Japanese Patent application No. 2005-171310, filed Jun. 10, 2005, the contents of which are incorporated herein by reference in their entireties.

BACKGROUND OF THE INVENTION

1. Field of the Invention

The present invention relates to an optical characteristic measuring apparatus for obtaining an optical characteristic of a measuring object, particularly a transfer function matrix (for example, Jones matrix) of a measuring object, in details, relates to an optical characteristic measuring apparatus capable of accurate measurement even when a frequency difference of a first and second incident lights is varied.

The present invention relates to an optical characteristic measuring apparatus having an interference section for multiplexing a first input light and a second input light, frequencies of which differ from each other and polarized states of which are perpendicular to each other, inputting a multiplexed light to a measuring object, and making output light outputted from the measuring object interfere with at least one of the first input light and the second input light. The optical characteristic measuring apparatus obtains an optical characteristic of the measuring object, particularly, a transfer function matrix (for example, Jones matrix) of the measuring object by interference light from the interference section. In details, the present invention relates to an optical characteristic measuring apparatus capable of accurate measurement even when a frequency sweep speed of a waveform variable light source is not constant.

The present invention relates to an optical characteristic measuring apparatus for measuring an optical characteristic of a measuring object, particularly a transfer function matrix (for example, Jones matrix) of the measuring object, by branching light from a light source section, making one branched light incident on the measuring object, and making output light (signal light) outputted from the measuring object interfere with other branched light (reference light).

In details, the present invention relates to an optical characteristic measuring apparatus capable of easily determining an increase or a decrease of a phase difference of light (signal light and reference light) to be multiplexed.

2. Description of the Related Art

An optical characteristic measuring apparatus obtains optical characteristics (for example, insertion loss, reflectance, transmittance, polarized light dependency, wavelength dispersion, polarization mode dispersion, and the like) of a measuring object (for example, optical element, optical apparatus, test apparatus/measuring apparatus of the optical element or the optical apparatus or the like), specifically obtains a transfer function matrix (for example, Jones matrix) of a measuring object by measurement, and obtains the optical characteristics of the measuring object all together, or only the necessary optical characteristic from the transfer function.

In order to obtain the transfer function matrix by measurement, signal light having a frequency fs is made to be incident on the measuring object, and signal light (transmitted light or reflected light) outputted from the measuring object is multiplexed with reference light (frequency fr) to interfere with each other. Further, an interference signal is received by a light receiving section and an amplitude and a phase of the interference signal are measured (so-to-speak heterodyne detection). Further, in order to obtain a transfer function in a predetermined measuring wavelength range, a light source is subjected to wavelength sweep (frequency sweep) (refer to, for example, JP-A-2002-243585, U.S. Pat. No. 6,376,830, and JP-A-2004-20567).

FIG. 14 is a diagram showing an input/output characteristic to and from a measuring object 1. In FIG. 14, input light, output light to and from the measuring object 1 are represented by a column vector of 2 columns and 1 row (so-to-speak Jones vector) representing amplitudes and phases of two polarized light perpendicular to each other, and a transfer function matrix (so-to-speak Jones matrix) of the measuring object 1 is shown by Equation (1) as follows.

[Equation 1]

$$\begin{pmatrix} T_{11} & T_{12} \\ T_{21} & T_{22} \end{pmatrix} \qquad (1)$$

In order to obtain such Jones matrix, first, second input light having polarized light (linearly polarized light, elliptically polarized light, circularly polarized light) polarized states of which are perpendicular to each other are inputted to the measuring object 1. Further, the amplitudes and phases of Jones vector of input light and output light outputted from the measuring object 1 are measured to obtain.

In order to easily obtain Jones matrix by operation from a result of measuring input light, output light, generally, linearly polarized light (for example, s polarized light, p polarized light) polarization planes of which are perpendicular to each other are used for the first, the second input light. Further, polarized states of respective input light of s polarized light, p polarized light to the measuring object 1 are changed by an optical characteristic of the measuring object 1 and emitted. Further, in order to facilitate the operation, in the output light from the measuring object 1, linearly polarized light (for example, s polarized light, p polarized light) polarization planes of which are perpendicular to each other are interfered with reference light to be measured.

That is, there are present emitted s polarized light and emitted p polarized light with regard to incident s polarized light, and there are present emitted s polarized light and emitted p polarized light with regard to incident p polarized light. Further, the incident s polarized light is s polarized light inputted to the measuring object 1, and the emitted s polarized light is s polarized light outputted from the measuring object 1. Also incident p polarized light, emitted p polarized light are similarly p polarized light inputted and outputted to and from the measuring object 1.

Therefore, in Equation (1), mentioned above, notation $T_{11}$ represents a relationship of emitted s polarized light relative to incident s polarized light, notation $T_{21}$ represents a relationship of emitted p polarized light relative to the incident s polarized light, notation $T_{12}$ represents a relationship of emitted s polarized light relative to incident p polarized light, notation $T_{22}$ represents a relationship of emitted p polarized light relative to incident p polarized light. That is, in notation $T_{xy}$, x represents a polarized state of an emitting side (x=1 represents s polarized light, x=2 represents p polarized light), y represents a polarized state of the incident side (y=1 represents s polarized light, y=2 represents p polarized light).

For example, when input light (that is, signal light) to the measuring object 1 is s polarized light, output light from the measuring object 1 becomes light multiplexed with $T_{11}$ and $T_{21}$ and becomes light multiplexed with $T_{12}$ and $T_{22}$ when input light is p polarized light.

In this way, it is necessary to measures polarized light, p polarized light having different polarization planes as input light and therefore, in a measuring method, there are a case in which measurement is carried out by subjecting input light to wavelength sweep by s polarized light and thereafter subjecting input light to wavelength sweep by p polarized light again, and a case in which measurement is carried out by one time wavelength sweep by simultaneously inputting s polarized light and p polarized light to the measuring object 1. When measured by one time wavelength sweep, a measuring time period can be shortened and measurement can be carried out accurately without an error derived from reproducibility (for example, wavelength reproducibility) in a first time and a second time of wavelength sweep.

However, since s polarized light and p polarized light are simultaneously inputted to the measuring object 1, it is necessary to separate an interference signal of s polarized light and reference light and an interference signal of p polarized light and reference light. In the separation, there are a method of separating by a time region by making the interference signal of s polarized light and the interference signal of p polarized light respectively constitute different measuring optical path difference (refer to, for example, U.S. Pat. No. 6,376,830), and a method of subjecting the interference signal of s polarized light and interference signal of p polarized light to intensity modulation respectively by different frequencies to separate from a difference in modulated frequencies for intensity modulation (refer to, for example, JP-A-2004-20567).

However, it is very difficult to separate the interference signal based on s polarized light and the interference signal based on p polarized light by the time region, when separated by the difference in the modulated frequencies, there poses a problem that a measured wavelength range is limited by wavelength dependency of an intensity modulator per se and the intensity modulator is very expensive.

[First Related Art]

FIG. 15 is a diagram showing a configuration of an optical characteristic measuring apparatus of a related art (refer to, for example, JP-A-2002-243585). In FIG. 15, a wavelength variable light source 2 outputs laser light while carrying out wavelength sweep by a predetermined wavelength sweep speed.

A half mirror (hereinafter, abbreviated as HM) 3 branches laser light from the wavelength variable light source 2 in two. A polarization beam splitter (hereinafter, abbreviated as PBS) 4 braches laser light in two of light (p polarized light, s polarized light) polarization planes of which are perpendicular to each other. Here, p polarized light is transmitted by an optical path OP1, and s polarized light is transmitted by an optical path OP2.

PBS 5 synthesizes light branched by PBS 4 and transmitted by the different optical paths OP1, OP2 to output to the measuring object 1. Here, light inputted to the measuring object 1 is signal light. A delay fiber 6 is provided on the optical path OP2 between PBS 4, 5 and delays one branched light.

Therefore, since incident s polarized light passes through the delay fiber 6, when a frequency of incident p polarized light is designated by notation f1 (t), a frequency of incident s polarized light becomes f2 (t) (f2 (t)≠f1 (t)). Here, respective f1 (t), f2 (t) are designated by notations f1, f2 as follows.

HM 7 synthesizes output light from the measuring object 1 and other light branched by HM 3 and transmitted by an optical path OP3. Here, light transmitted by the optical path OP3 is reference light. PBS 8 branches light multiplexed by HM 7 in 2 of light polarization planes of which are perpendicular to each other.

A light receiving section 9 receives one light (for example, p polarized light) branched by PBS 8. A light receiving section 10 receives other light (for example, s polarized light) branched by PBS 8. A light receiving section 11 receives light multiplexed by PBS 5. Further, PBS 5 receives light from a plane different from that emitted to the measuring object 1.

Therefore, at the light receiving section 9, three kinds of light of reference light (frequency f1'), emitted light polarized light (frequencies f1, f2) are interfered with each other. Further, reference light is provided with a frequency f1' different from that of signal light, which is produced by an optical length difference of an optical path branched by HM 3 to the optical path OP1, PBS 5, the measuring object 1, HM 7 and an optical path of the optical path OP3, and the optical path length difference is sufficiently smaller than an optical path length difference of the optical path OP1 and the optical path OP2 including the delay fiber 6. Therefore, a relationship of the frequency difference is represented by $|f1'-f2| \gg |f1'-f1|$.

Naturally, when the optical path difference between the optical path branched by HM 3 to the optical path OP1, PBS 5, the measuring object 1, HM 7 and the optical path of the optical path OP3=0, the frequency f1=f1'.

Operation of the apparatus will be explained.

The wavelength variable light source 2 carries out wavelength sweep (frequency sweep) by a predetermined sweep speed. Further, HM 3 branches laser light from the wavelength variable light source in two. Further, a polarized wave controller, not illustrated, between the wavelength variable light source 2 and HM 3 pertinently controls polarized light such that laser light is branched in two at PBS 4.

Further, PBS 4 branches laser light to be multiplexed by PBS 5 by way of the optical paths OP1, OP2. One of multiplexed light is outputted to the measuring object 1 and other thereof is received by the light receiving section 11.

HM 7 synthesizes output light (signal light) from the measuring object 1 and other light (reference light) from the optical path OP3. Further, PBS 8 branches multiplexed interference light to two of linearly polarized light polarization planes of which are perpendicular to each other. Further, one light branched by PBS 8 is received by the light receiving section 9, other light is received by the light receiving section 10.

Further, filtering is carried out by a filter, not illustrated, at a rear stage and Jones matrix of the measuring object 1 is obtained by calculating section, not illustrated. As objects to be filtered, for example, at the light receiving section 9, there are present emitted p polarized light of frequencies f1, f2 and an interference signal by reference light of the frequency f1'.

Therefore, in order to obtain respective elements of Jones matrix by an output signal from the light receiving section 9, it is necessary to extract an interference signal of emitted p polarized light of the frequency f1 and reference light of the frequency f1' and extract an interference signal of emitted p polarized light of the frequency f2 and reference light of the frequency f1'. Therefore, by a low-pass filter for passing a vicinity of a direct current component and a band-pass filter for passing a vicinity of a frequency difference |f1'−f2|, predetermined interference signals are provided and outputted to calculating section, not illustrated, at the rear stage. Further, the calculating section obtains Jones matrix. Further, by an output of the light receiving section 11, nonlinearity of wavelength sweep of the wavelength variable light source 2 is corrected.

[Second Related Art]

FIG. 16 is a diagram showing a configuration of an optical characteristic measuring apparatus of a second related art (refer to, for example, JP-A-2002-243585). In FIG. 16, a wavelength variable light source 2 outputs laser light while carrying out wavelength sweep by a predetermined wavelength sweep speed. A half mirror (hereinafter, abbreviated as HM) 3 branches laser light from the wavelength variable light source 2 in two.

A polarized light delay section 6*c* includes polarization beam splitters (hereinafter, abbreviated as PBS) 4*a*, 4*b*, and a delay fiber 6 for generating incident p polarized light, incident s polarized light from one laser light branched by HM 3.

PBS 4*a* branches laser light in two of light (p polarized light, s polarized light) polarization planes of which are perpendicular to each other. Here, p polarized light is transmitted by an optical path OP1 and s polarized light is transmitted by an optical path OP2. PBS 4*b* multiplexes light branched by PBS 4*a* and transmitted by the different optical paths OP1, OP2 to be outputted to a measuring object 1. Here, light inputted to the measuring object 1 is signal light. The delay fiber 6 is provided on the optical path OP2 between PBS 4*a*, 4*b* to delay s polarized light.

Therefore, since incident s polarized light passes through the delay fiber 6, when a frequency of incident p polarized light is designated by notation f1 (t), a frequency of incident s polarized light becomes f2 (t) (f2 (t)≠f1 (t)). Here, respective f1 (t), f2 (t) are designated by notations f1, f2 as follows.

HM 7 multiplexes output light from the measuring object 1 and other light branched by HM 3 and transmitted by an optical path OP3 to be interfered with each other. Here, light transmitted by the optical path OP3 is reference light. PBS 8 branches light multiplexed by HM7 into two of light polarization planes of which are perpendicular to each other.

A light receiving section 9 receives one light (for example, s polarized light) branched by PBS 8. A light receiving section 10 receives other light (for example, p polarized light) branched by PBS 8.

Therefore, explaining of the light receiving section 9, three kinds of light of the reference light (frequency f1'), emitted s polarized light (frequencies f1, f2) are interfered with each other. Further, the reference light is provided with a frequency f1' different from that of the signal light owing to an optical path length difference between the signal light and the reference light.

That is, there is brought about an optical path length difference between an optical path branched by HM 3 to the optical path OP1, PBS 4*b*, the measuring object 1, HM 7 and the optical path OP3, the optical path length difference is sufficiently smaller than an optical path length difference between the optical path OP1 and the optical path OP2 including the delay fiber 6. Therefore, a relationship of a frequency difference is (|f1'−f2|>>|f1'−f1|).

Similarly, at the light receiving section 10, three kinds of light of the reference light (frequency f1'), emitted p polarized light (frequencies f1, f2) are interfered with each other.

Naturally, when the optical path difference between the optical path branched by HM 3 to the optical path OP1, PBS 4*b*, the measuring object 1, HM 7 and the optical path of the optical path OP3=0, the frequency f1=f1'.

Filter circuits 101, 102 are provided at a rear stage of the light receiving sections 9, 10 for subjecting signals from the light receiving section 9, 10 to low pass, band pass filtering. Calculating section 103 is inputted with signals filtered by the filter circuits 101, 102, (signal after low pass filtering and signal after band pass filtering).

Operation of the apparatus will be explained.

The wavelength variable light source 2 carries out wavelength sweep (frequency sweep) by a predetermined sweep speed. Further, HM 3 branches laser light from the wavelength variable light source in two. Further, a polarized wave controller, not illustrated, between the wavelength variable light source 2 and HM 3 pertinently controls polarized light such that laser light is branched in two at PBS 4*a*.

Further, p polarized light, s polarized light transmitted by the optical paths OP1, OP2 to produce the frequency difference are multiplexed by PBS 4*b* to be outputted to the measuring object 1.

HM 7 multiplexes output light (signal light) from the measuring object 1 with other light (reference light) transmitted by the optical path OP3. Further, PBS 8 branches multiplexed interference light to two of linearly polarized light polarization planes of which are perpendicular to each other. Further, one light branched by PBS 8 is received by the light receiving section 9 and other light is received by the light receiving section 10.

Further, respective the filter circuits 101, 102 output signals from the light receiving sections 9, 10, or signals subjected to lowpass filtering, signals subjected to bandpass filtering to the calculating section 103. Further, the calculating section 103 obtains Jones matrix of the measuring object 1 from an amplitude and a phase of an interference signal after having been filtered.

Further, as signals to be filtered by the filter circuit 101, for example, at the light receiving section 9, there is present an interference signal by emitted s polarized light of frequencies f1, f2 and reference light (s polarized light) of the frequency f1'.

Therefore, in order to obtain respective elements of Jones matrix by an output signal from the light receiving section 9, it is necessary to extract an interference signal of emitted s polarized light (frequency f1) and the reference light (frequency f1') and extract an interference signal of emitted s polarized light (frequency f2) and the reference light (frequency f1').

Hence, the filter circuit 101 carries out the separation by a low-pass filter for passing a vicinity of a direct current component and a band-pass filter for passing a vicinity of the frequency difference (|f1'−f2|) and outputs the separated interference signal to the calculating section 103.

Similarly, as signals to be filtered by the filter circuit 102, for example, at the light receiving section 10, there is present an interference signal by emitted p polarized light of frequencies f1, f2 and the reference light of the frequency f1'.

Therefore, in order to obtain respective elements of Jones matrix by the output signal from the light receiving section 10, it is necessary to obtain an interference signal of emitted p polarized light (frequency f1) and the reference light (frequency f1') and extract the interference signal of emitted p polarized light (frequency f2) and the reference light (frequency f1').

Hence, the filter circuit 102 carries out the separation by the low-pass filter for passing a vicinity of a direct current component and the band-pass filter for passing a vicinity of the frequency difference (|f1'−f2|) and outputs the separated interference signal to the calculating section 103. Further, the calculating section 103 obtains Jones matrix from the interference signals from the filter circuits 101, 102.

[Third Related Art]

FIG. 17 is a diagram showing a configuration of an optical characteristic measuring apparatus of a third related art.

A wavelength variable light source 2 outputs laser light while carrying out wavelength sweep by a predetermined wavelength sweep speed. An optical fiber 366 transmits laser light from the wavelength variable light source 2. A lens 466 makes laser light emitted from the optical fiber 366 parallel light. A polarized wave controller 566 converts parallel light from the lens 466 to a desired polarized state (for example, linearly polarized light).

An interference section 666 includes a half mirror (hereinafter, abbreviated as HM) 666a, mirrors 666b, 666c, a polarization beam splitter (hereinafter, abbreviated as PBS) 666d, a polarization plane rotating section 666e, polarizers 666f, 666g, branches light from the polarized wave controller 566, inputs one branched light to the measuring object 1, and makes output light (signal light) outputted from the measuring object 1 interfere with other branched light (reference light).

HM 666a is a branching section for branching parallel light from the polarized wave controller 566 without depending on the polarized state, and outputs one branched light to the measuring object. The mirrors 666b, 666c are arranged on an optical path of other branched light branched by HM 666a, and successively reflect reference light.

PBS 666d is arranged on an optical path of output light from the measuring object 1, multiplexes reflected light (reference light) from the mirror 666c and signal light to be branched in two of light polarization planes of which are orthogonal to each other.

The polarization plane rotating section 666e is, for example, a ½ wave plate or the like, and provided between the mirror 666b and the mirror 666c. The polarizer 666f is provided on an optical path of one branched light from PBS 666d, and the polarizer 666g is provided on an optical path of other branched light from PBS 666d for making signal light and reference light interfere with each other.

A photodiode 766 receives interference light from the polarizer 666f of the interference section 666 and outputs a signal in accordance with optical power (also referred to as optical intensity) of received interference light. A photodiode 866 receives other interference light from the polarizer 666g of the interference section 666 and outputs a signal in accordance with the optical power of received interference light. A calculating section 966 is inputted with interference signals from the photodiodes 766, 866.

Operation of the apparatus will be explained.

In order to input respective p polarized light and s polarized light to the measuring object 1, wavelength sweep is carried out twice in a predetermined wavelength range. An explanation will be given from the first wavelength sweep.

The wavelength variable light source 2 outputs laser light while continuously carrying out wavelength sweep in a predetermined wavelength range. Further, the lens 466 makes laser light transmitted by the optical fiber 366 parallel light, and the polarized wave controller 566 converts a polarized state of laser light made to be parallel light into p polarized light to be outputted to the interference section 666.

Further, HM 666a branches light from the polarized wave controller 566, outputs one thereof to the measuring object 1 as signal light and outputs other thereof to the mirror 666b as reference light. Further, the polarization plane rotating section 666e inclines a polarization plane of reflected light from the mirror 666b by 45° to be outputted to the mirror 666c such that optical power is uniformly branched at PBS 666d at a rear stage.

Further, PBS 666d multiplexes output light (emitted s polarized light, emitted p polarized light in correspondence with incident p polarized light) from the measuring object 1 and reference light by way of the mirrors 666b, 666c to be branched in two of light (p polarized light, s polarized light) polarization planes of which are orthogonal to each other and outputs emitted p polarized light to the photodiode 766 and outputs emitted s polarized light to the photodiode 866. Further, polarization planes of light (signal light and reference light) multiplexed and branched by PBS 666d are orthogonal to each other and therefore, the light is received by the photodiodes 766, 866 by inclining polarization planes by the polarizers 666f, 666g.

Thereby, the photodiode 766 is inputted with interference light of signal light operated by $T_{22}$ of Jones matrix and reference light. Further, the photodiode 866 is inputted with interference light of signal light operated by $T_{12}$ of Jones matrix and reference light.

Further, the photodiodes 766, 866 output electric signals in accordance with optical power of received interference light to the calculating section 966.

Successively, second wavelength sweep is carried out and a point of the second wavelength sweep which differs from the first wavelength sweep resides in that the polarized wave controller 566 converts laser light to s polarized light, that the photodiode 766 is inputted with interference light of signal light operated by $T_{21}$ of Jones matrix and reference light, and that the photodiode 866 is inputted with interference light of signal light operated by T11 of Jones matrix and reference light, the other operation is similar to that of the first wavelength sweep and therefore, an explanation thereof will be omitted.

Further, the calculating section 966 calculates respective elements of Jones matrix from phases and amplitudes of interference signals based on respective p polarized light, polarized light to thereby calculate an optical characteristic of the measuring object 1 from calculated Jones matrix.

[With Respect to the First Related Art]

In the apparatus shown in FIG. 15, the frequency difference (|f1−f2|) of incident p polarized light, incident polarized light is determined by the optical path length difference of the optical paths OP1, OP2 and the wavelength sweep speed (frequency sweep speed), and also a frequency of a high frequency component of the interference signal is determined.

Therefore, the signal outputted from the light receiving section is separated into an interference signal of a high frequency component (several tens through several hundreds [MHz]) and an interference signal of a direct current through low frequency component (which is sufficiently lower than the high frequency component and is, for example, about DC through 200 [kHz]).

However, it is very difficult currently to subject a total wavelength range to wavelength sweep with linearity. Therefore, owing to nonlinearity of wavelength sweep, there poses a problem that a wavelength difference (frequency difference |f1−f2|) of p polarized light, s polarized light passing through the optical paths OP1, OP2 does not stay to be constant, the frequency of the high frequency component of the interference signal is varied and it is difficult to accurately obtain the optical characteristic.

Further, since the signal of the high frequency component is dealt with, in comparison with a case of dealing with the signal of the low frequency component, there poses a problem that circuit design of the band-pass filter for passing only the high frequency component, an electric circuit at a rear stage of filter and the like is difficult, and a circuit configuration becomes complicated.

[With Respect to the Second Related Art]

According to the apparatus shown in FIG. 16, the frequency difference (|f1−f2|) of incident p polarized light, incident polarized light is determined by the optical length difference of the optical path OP1, OP2 and a wavelength sweep speed (frequency sweep speed) and also the frequencies of the interference signals are determined.

Therefore, by filtering the signals outputted from the light receiving sections 9, 10 by the filter circuits 101, 102, an interference signal of a high frequency component (several tens through several hundreds [MHz]) and an interference signal of a direct current through a low frequency component (which is sufficiently lower than the high frequency component and is, for example, about DC through 200 [kHz]) can be separated.

However, it is currently very difficult for the wavelength variable light source 2 to subject a total measuring wavelength range to wavelength sweep with linearity. Therefore, owing to nonlinearity of wavelength sweep, a wavelength difference (frequency difference |f1−f2|) of p polarized light, s polarized light respectively passing through the optical paths OP1, OP2 does not stay to be constant, frequencies of the interference signals are varied to pose a problem that it is difficult to accurately obtain an optical characteristic unless characteristics of the low-pass filter, the band-pass filter are changed (for example, passing frequency bands are made variable).

[With Respect to the Third Related Art]

Jones matrix of the measuring object 1 is calculated from phases and amplitudes of interference signals of signal light and reference light.

However, generally, with regard to a light wave interference signal measured by the photodiodes 766, 866, signal intensity proportional to a trigonometric function of a phase difference of multiplexed light (signal light, reference light) is obtained to pose a problem that it is difficult to determine whether the phase difference is increased or decreased.

Therefore, for example, in U.S. Pat. No. 6,376,830, there is constructed a configuration in which the phase difference of signal light and reference light is only increased or decreased by bringing the optical path of transmitting signal light, the optical path of transmitting reference light, the optical path of the measuring object 1 under a predetermined condition. Therefore, there poses a problem that a configuration of the optical characteristic measuring apparatus is significantly restricted, that is, an optical path length of the measuring object 1 is limited.

SUMMARY OF THE INVENTION

The present invention has been made in view of the above circumstances, and provides an optical characteristic measuring apparatus capable of accurate measurement even when a frequency difference of first and second input lights is varied.

Further, the present invention provides an optical characteristic measuring apparatus capable of accurate measurement even when a frequency sweep speed of a wavelength variable light source is not constant.

Further, the present invention provides an optical characteristic measuring apparatus capable of easily determining an increase or a decrease of a phase difference of light (signal light and reference light) to be multiplexed.

In some implementations, an optical characteristic measuring apparatus of the invention for measuring an optical characteristic of a measuring object comprises:

a light source section which sweeps wavelengths of a first input light and a second input light respectively, frequencies of the first input light and the second input light being different from each other and polarized states of the first input light and the second input light being perpendicular to each other, and outputs the first input light and the second input light;

an interference section which branches each of the first input light and the second input light from the light source section, inputs one branched light to the measuring object, makes output light from the measuring object interfere with other branched light, and outputs a plurality of interference lights;

a plurality of light receiving sections which are respectively provided for the interference lights outputted from the interference section, receives the interference lights respectively, and outputs signals in accordance with optical powers of the interference lights respectively; and a low-pass filter for filtering the signals outputted from the light receiving sections, wherein the plurality of interference lights includes:

a first interference light in which the first input light interferes with an output light in a first polarized state of the output light from the measuring object;

a second interference light in which the second input light interferes with the output light in the first polarized state of the output light from the measuring object;

a third interference light in which the first input light interfere with an output light in a second polarized state of the output light from the measuring object; and a fourth interference light in which the second input light interferes with the output light in the second polarized state of the output light from the measuring object, and the first polarized state of the output light and the second polarized state of the output light are perpendicular to each other.

According to the optical characteristic measuring apparatus, the interference section outputs the interference light of the first input light and the light in the first polarized state in the output light of the measuring object (the output light in correspondence with the first and the second input light), the interference light of the second input light and the light in the first polarized state in the output light of the measuring object, the interference light of the first input light and the light in the second polarized state (perpendicular to the first polarized state) in the output light of the measuring object, and the interference light of the second input light and the light in the second polarized state in the output light (the output light in correspondence with the first and the second input light) of the measuring object. Further, a signal based on the interference light is filtered by the low-pass filter. Thereby, an interference signal of the a low frequency component passing through the low-pass filter is not influenced by the difference of the frequencies of the first and the second input light produced by nonlinearity of frequency sweep of the light source section. Therefore, even when the difference of the frequencies of the first and the second input light is varied, the interference signal can accurately be measured. Further, only the signal of the low frequency component is dealt with and therefore, circuit design of the low-pass filter, an electric circuit at a rear stage of the filter and the like is facilitated and a circuit configuration is simplified.

In the optical characteristic measuring apparatus of the invention, the low-pass filter passes a signal having a frequency lower than a difference of the frequencies of the first input light and the second input light which are outputted from the light source section.

In the optical characteristic measuring apparatus of the invention, the first input light and the second input light are linearly polarized lights.

In the optical characteristic measuring apparatus of the invention, the interference section includes:

a multiplexing section for multiplexing the first input light and the second input light from the light source section;

an input light branching section for branching a multiplexed light and outputting one branched light to the measuring object;

a first polarization beam splitter for branching the output light from the measuring object;

a second polarization beam splitter for multiplexing and branching one branched light of the first polarization beam splitter and other branched light of the input light branching section;

a third polarization beam splitter for multiplexing and branching other branched light of the first polarization beam splitter and other branched light of the input light branching section; and a plurality of polarizers which are provided for branched lights of the second polarization beam splitter and branched lights of the third polarization beam splitter respectively, and respectively makes multiplexed lights of the branched lights of the second polarization beam splitter and multiplexed lights of the branched lights of the third polarization beam splitter interfere.

In the optical characteristic measuring apparatus of the invention, the interference section includes:

a first input light branching section for branching the first input light;

a second input light branching section for branching the second input light;

a multiplexing section for multiplexing one branched light from the first input light branching section and one branched light from the second input light branching section so as to output a multiplexed light to the measuring object;

an output light branching section for branching the output light from the measuring object;

a first polarization beam splitter for multiplexing and branching one branched light of the output light branching section and other branched light of the first input light branching section;

a second polarization beam splitter for multiplexing and branching other branched light of the output light branching section and other branched light of the second input light branching section; and a plurality of polarizers which are provided for branched lights of the first polarization beam splitter and branched lights of the second polarization beam splitter respectively, and respectively makes multiplexed lights of the branched lights of the first polarization beam splitter and multiplexed lights of the branched lights of the second polarization beam splitter interfere.

In the optical characteristic measuring apparatus of the invention, the interference section includes:

a first input light branching section for branching the first input light;

a second input light branching section for branching the second input light;

a multiplexing section for multiplexing one branched light from the first input light branching section and one branched light from the second input light branching section so as to output a multiplexed light to the measuring object;

an output light branching section for branching the output light from the measuring object;

a first output light multiplexing section for multiplexing one branched light of the output light branching section and other branched light of the first input light branching section so as to make the one branched light of the output light branching section interfere with the other branched light of the first input light branching section;

a first polarization beam splitter for branching interference light of the first output light multiplexing section;

a second output light branching section for multiplexing other branched light of the output light branching section and other branched light of the second input light branching section so as to make the other branched light of the output light branching section interfere with the other branched light of the second input light branching section; and a second polarization beam splitter for branching interference light of the second output light multiplexing section.

In the optical characteristic measuring apparatus of the invention, the first output light multiplexing section and the second output light multiplexing section are commonly provided in one section.

Accordingly, the first and the second output light multiplexing sections are made common and therefore, a number of parts is reduced to achieve small-sized formation, facilitating alignment, a reduction in cost.

In the optical characteristic measuring apparatus of the invention, the first input light branching section and the second input light branching section are commonly provided in one section.

Accordingly, the first and the second input light branching sections are made common and therefore, a number of parts is reduced to achieve small-sized formation, facilitating alignment, a reduction in cost.

In the optical characteristic measuring apparatus of the invention, the first polarization beam splitter and the second polarization beam splitter are commonly provided in one polarization beam splitter.

Accordingly, the first and the second polarization beam splitters are made common and therefore, a number of parts is reduced to achieve small-sized formation, facilitating alignment, a reduction in cost.

The optical characteristic measuring apparatus of the invention further comprises:

a plurality of polarizers which is provided for branched lights of the first polarization beam splitter and branched lights of the second polarization beam splitter respectively, and respectively passes only interference lights having a predetermined polarization plane.

Accordingly, the polarizer passes only light of a predetermined polarization plane to be outputted to the light receiving section and therefore, noise of the interference signal can be reduced.

In the optical characteristic measuring apparatus of the invention, the interference section is an interferometer of a spatial light type.

Accordingly, by constituting the interference section by the interferometer of the spatial light type, an optical system can be downsized and is made to be strong at vibration.

In some implementations, an optical characteristic measuring apparatus of the invention for measuring an optical characteristic of a measuring object comprises:

a first wavelength variable light source which sweeps a wavelength of a first input light and outputs the first input light to an interference section;

a second wavelength variable light source which sweeps a wavelength of a second input light and outputs the second input light to the interference section, frequencies of the first input light and the second input light being different from each other and polarized states of the first input light and the second input light being perpendicular to each other;

the interference section which multiplexes and inputs the first input light and the second input light to the measuring object, makes output light from the measuring object interfere with at least one of the first input light and the second input light, and outputs a plurality of interference lights;

a detecting section for detecting a frequency difference of the first input light and the second input light from the first wavelength variable light source and the second wavelength variable light source; and a control section for controlling a frequency difference of the first wavelength variable light source and the second wavelength variable light source based on the frequency difference detected by the detecting section.

Accordingly, the detecting section detects the frequency difference of light outputted from the first and the second wavelength variable light sources, the control section controls the wavelength sweep speed of the at least one of the first and the second wavelength variable light sources based on the frequency difference detected by the detecting section and therefore, one light source is subjected to wavelength sweep while maintaining the constant light frequency difference relative to other light source. Thereby, a center frequency of the interference light outputted from the interference section is not varied. Therefore, the optical characteristic of the measuring object can accurately be measured even when the wavelength sweep speed of the wavelength variable light source is not constant.

In some implementations an optical characteristic measuring apparatus of the invention for measuring an optical characteristic of a measuring object comprises:

a wavelength variable light source which sweeps a wavelength of a laser light and outputs the laser light;

a branching section which branches the laser light from the wavelength variable light source and outputs one branched light to an interference section as a first input light;

the interference section which multiplexes and inputs the first input light and a second input light to the measuring object, makes output light from the measuring object interfere with at least one of the first input light and the second input light, and outputs a plurality of interference lights, frequencies of the first input light and the second input light being different from each other and polarized states of the first input light and the second input light being perpendicular to each other; and an acousto-optical modulator which shifts a frequency of other branched light from the branching section for a predetermined amount and outputs the frequency-shifted other branched light to the interference section as the second input light.

Accordingly, the acousto-optical modulator shifts the laser light outputted from the wavelength variable light source by a predetermined amount to be outputted to the interference section and therefore, the interference section is inputted with the first and the second input light maintaining the constant light frequency difference. Thereby, the center frequency of the interference light outputted from the interference section is not varied. Therefore, the optical characteristic of the measuring object can accurately be measured even when the wavelength sweep speed of the wavelength variable light source is not constant.

In the optical characteristic measuring apparatus of the invention, at least one of the first wavelength variable light source and the second wavelength variable light source includes a vertical-cavity surface-emitting laser (VCSEL) forming a resonator by a movable mirror being formed by a semiconductor micromachining technology.

In the optical characteristic measuring apparatus of the invention, the wavelength variable light source includes a vertical-cavity surface-emitting laser (VCSEL) forming a resonator by a movable mirror being formed by a semiconductor micromachining technology.

Accordingly, the wavelength variable light source outputs the laser light by using the vertical-cavity surface-emitting laser (VCSEL) forming the resonator by the movable mirror formed by the semiconductor micromachining technology and therefore, cost can be reduced and the wavelength sweep speed can be accelerated. Thereby, a number of times of wavelength sweep is increased in a predetermined time period and an averaging processing can be increased and an accuracy of measurement is promoted. Further, although the interferometer of the interference section is much liable to be effected with an influence of disturbance (vibration), by shortening the wavelength sweep time period, the influence of disturbance can be restrained and the accuracy of measurement is promoted.

In the optical characteristic measuring apparatus of the invention, at least one of the first wavelength variable light source and the second wavelength variable light source includes a surface emitting laser forming a resonator by a movable mirror being formed by a semiconductor micromachining technology, and the first wavelength variable light source and the second wavelength variable light source are provided on a same substrate.

Accordingly, the wavelength variable light source outputs the laser light by using the surface emitting laser forming the resonator by the movable mirror formed by the semiconductor micromachining technology and therefore, cost can be reduced and the wavelength sweep speed can be accelerated. Thereby, a number of times of wavelength sweep is increased in a predetermined time period and an averaging processing can be increased and an accuracy of measurement is promoted. Further, although the interferometer of the interference section is much liable to be effected with an influence of disturbance (vibration), by shortening the wavelength sweep time period, the influence of disturbance can be restrained and the accuracy of measurement is promoted.

In the optical characteristic measuring apparatus of the invention, the interference section includes a polarization beam splitter which multiplexes the first input light and the second input light and outputs a multiplexed light to the measuring object.

Accordingly, the polarization beam splitter of the interference section multiplexes the first and the second input light to be outputted to the measuring object and therefore, the first and the second input light can efficiently be multiplexed. Thereby, loss of optical power can be restrained and interference light having strong optical power can be provided.

In the optical characteristic measuring apparatus of the invention, the interference section includes:

a polarization beam splitter which multiplexes at least one of the first input light and the second input light with the output light from the measuring object, and branches a multiplexed light into s polarized light and p polarized light; and a polarization plane rotating section which inclines at least one polarization plane of the first input light and the second input light by 45°, and outputs an inclined light to the polarization beam splitter.

The optical characteristic measuring apparatus of the invention further comprising:

a plurality of light receiving sections which are respectively provided for the interference lights outputted from the interference section, receives the interference lights respectively, and outputs signals in accordance with optical powers of the interference lights respectively; and a low-pass filter for filtering the signals outputted from the light receiving sections, wherein the interference section branches each of the first input light and the second input light, inputs one branched light to the measuring object, makes the output light from the measuring object interfere with other branched light, and outputs the plurality of interference lights, the plurality of interference lights includes:

a first interference light in which the first input light interferes with an output light in a first polarized state of the output light from the measuring object;

a second interference light in which the second input light interferes with the output light in the first polarized state of the output light from the measuring object;

a third interference light in which the first input light interfere with an output light in a second polarized state of the output light from the measuring object; and a fourth interference light in which the second input light interferes with the output light in the second polarized state of the output light from the measuring object, and the first polarized state of the output light and the second polarized state of the output light are perpendicular to each other.

Accordingly, the interference section constitutes the interference signal for obtaining respective elements of Jones matrix by the interference signal of the low frequency to be outputted. Thereby, an influence of the frequency difference of the first and the second input light produced by nonlinearity of frequency sweep of the wavelength variable light source can further be alleviated. Therefore, even when the frequency difference of the first and the second input light is varied, the interference signal can accurately be measured. Further, only the signal of the low frequency component is dealt with and therefore, circuit design of the low-pass filter, an electric circuit or the like at a rear stage of the filter is facilitated and a circuit configuration is simplified.

In the optical characteristic measuring apparatus of the invention, the low-pass filter passes a signal having a frequency lower than a difference of the frequencies of the first input light and the second input light.

In the optical characteristic measuring apparatus of the invention, the interference section is an interferometer of a spatial light type.

Accordingly, by constituting the interference section by the interferometer of the spatial light type, the optical system can be downsized and is made to be strong at vibration.

In some implementations, an optical characteristic measuring apparatus of the invention for measuring an optical characteristic of a measuring object comprises:

an interference section which branches light from a light source section, inputs one branched light to the measuring object, and makes other branched light interfere with output light being outputted from the measuring object so as to form interference fringes by multiplexing the output light and the other branched light while inclining an optical axis of the output light and an optical axis of the other branched light, wherein a moving direction and a moving amount of the interference fringes are measured.

Accordingly, the interference fringes are formed by multiplexing the output light (signal light) of the measuring object and the other branched light (reference light) by shifting the optical axis of the other branched light relative to the optical axis of the output light (signal light) and the moving amount and the moving direction the interference fringes are measured. That is, the interference fringes are moved in a predetermined direction in accordance with an increase or a decrease in a phase difference of light (signal light and reference light) to be multiplexed. Thereby, the increase or the decrease in the phase difference of light to be multiplexed can easily be determined.

The optical characteristic measuring apparatus of the invention further comprises:

at least one photodiode array which includes a plurality of photodiodes and receives an interference light from the interference section, the photodiodes being arranged to be shifted along a direction in which the interference fringes are formed; and an interference signal converting section which generates an interference signal from an output of the photodiode array, a phase of the interference signal being shifted.

Accordingly, the interference section forms the spatial interference fringes by making the output light (signal light) and the branched light (reference light) interfere with each other by inclining the optical axis of the output light and the optical axis of the other branched light. Further, the light is received by the plurality of photodiodes the phase of which are shifted relative to the period of the interference fringes, and an interference signal converting section outputs the interference signals the phases of which are shifted from each other by 90° based on the output from the photodiode. Thereby, the moving direction and the moving amount the interference fringes are calculated and the increase or the decrease in the phase difference of light (signal light and reference light) to be multiplexed can easily be determined. Therefore, the optical path length of the measuring object is not restricted.

In the optical characteristic measuring apparatus of the invention, the plurality of photodiodes includes at least four photodiodes, and the respective photodiodes receive light by equally dividing one spatial period of the interference fringes by four.

In the optical characteristic measuring apparatus of the invention, the interference signal converting section outputs a subtraction result of an output of a third photodiode of the photodiodes and an output of a first photodiode of the photodiodes as a first interference signal, and the interference signal converting section outputs a subtraction result of an output of a fourth photodiode of the photodiodes and an output of a second photodiode of the photodiode as a second interference signal.

In the optical characteristic measuring apparatus of the invention, the at least one photodiode array includes a plurality of photodiode arrays which are arranged along a direction in which the interference fringes are formed.

Accordingly, the plurality of pieces of photodiode arrays are provided along the direction of aligning the interference fringes, and the interference signal converting section generates the interference signals from the outputs of the plurality of photodiode arrays. Thereby, even when a nonuniformity (random noise) is present at a section or a total of the interference fringes, the interference signal which is less influenced by the nonuniformity can be provided by averaging.

In the optical characteristic measuring apparatus of the invention, the plurality of photodiodes includes at least (4×n) photodiodes, the respective photodiodes receive light by equally dividing one spatial period of the interference fringes by four, the interference signal converting section outputs a subtraction result of an output of (4×(i−1)+3)-th photodiode of the photodiodes and an output of (4×(i−1)+1)-th photodiode of the photodiodes as a first interference signal, and the interference signal converting section outputs a subtraction result of an output of (4×(i−1)+4)-th photodiode of the photodiodes and an output of (4×(i−1)+2)-th photodiode of the photodiodes as a second interference signal, where notations n, i designate natural numbers.

Accordingly, the photodiode array measures the plurality of periods of interference fringes, and the interference signal converting section generates the interference signals from the outputs of the photodiode arrays. Thereby, even when there is a nonuniformity (random noise) at a section or a total of the interference fringes, the interference signals which are less influenced by the nonuniformity can be provided by averaging.

The optical characteristic measuring apparatus of the invention further comprises:

a correcting section for correcting a difference between a spatial period of the interference fringes and a period of the photodiodes of the photodiode array.

Accordingly, the correcting section corrects the error in the moving amount produced by the shift of the photodiode array of the spatial period of the interference fringes and therefore, the moving amount can accurately be measured.

DESCRIPTION OF THE PREFERRED EMBODIMENTS

An embodiment of the invention will be explained in reference to the drawings as follows.

Figure 1:
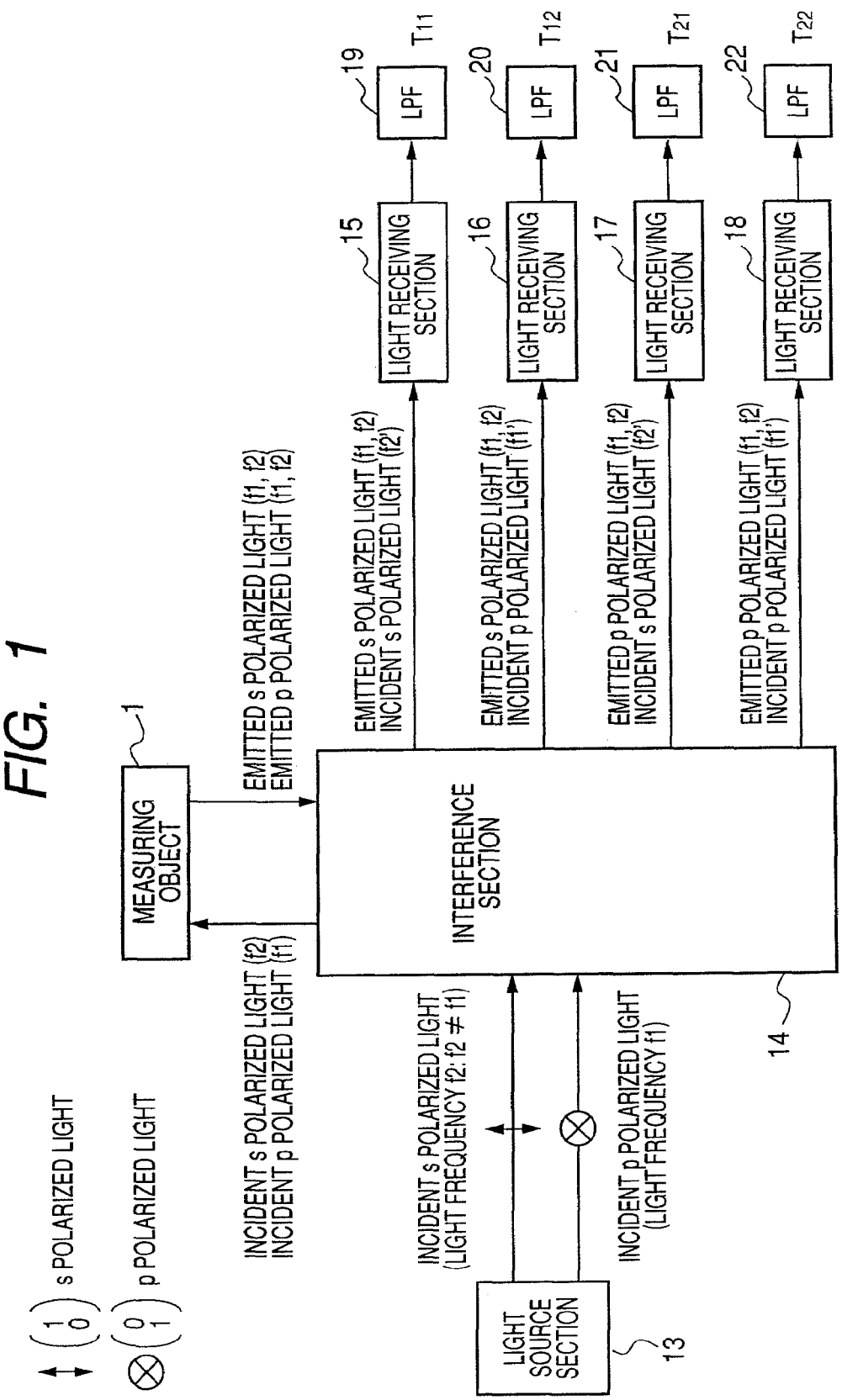
FIG. 1 is an entire configuration diagram of an apparatus showing a first embodiment of the invention.
Figure 14:
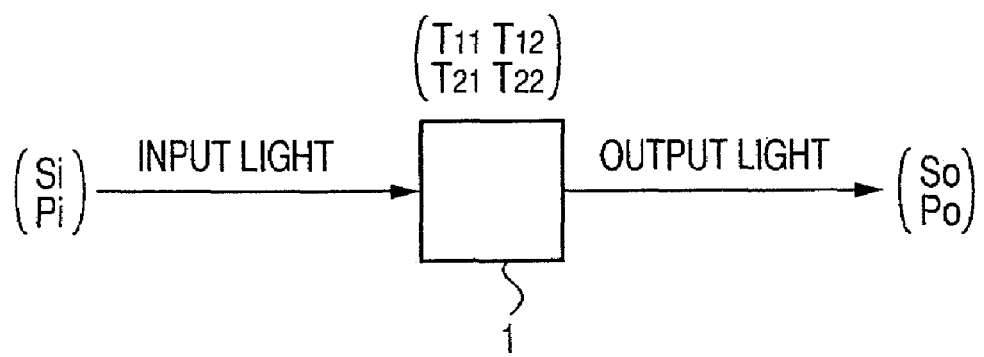
FIG. 14 is a diagram showing an input/output characteristic of a measuring object.
Figure 15:
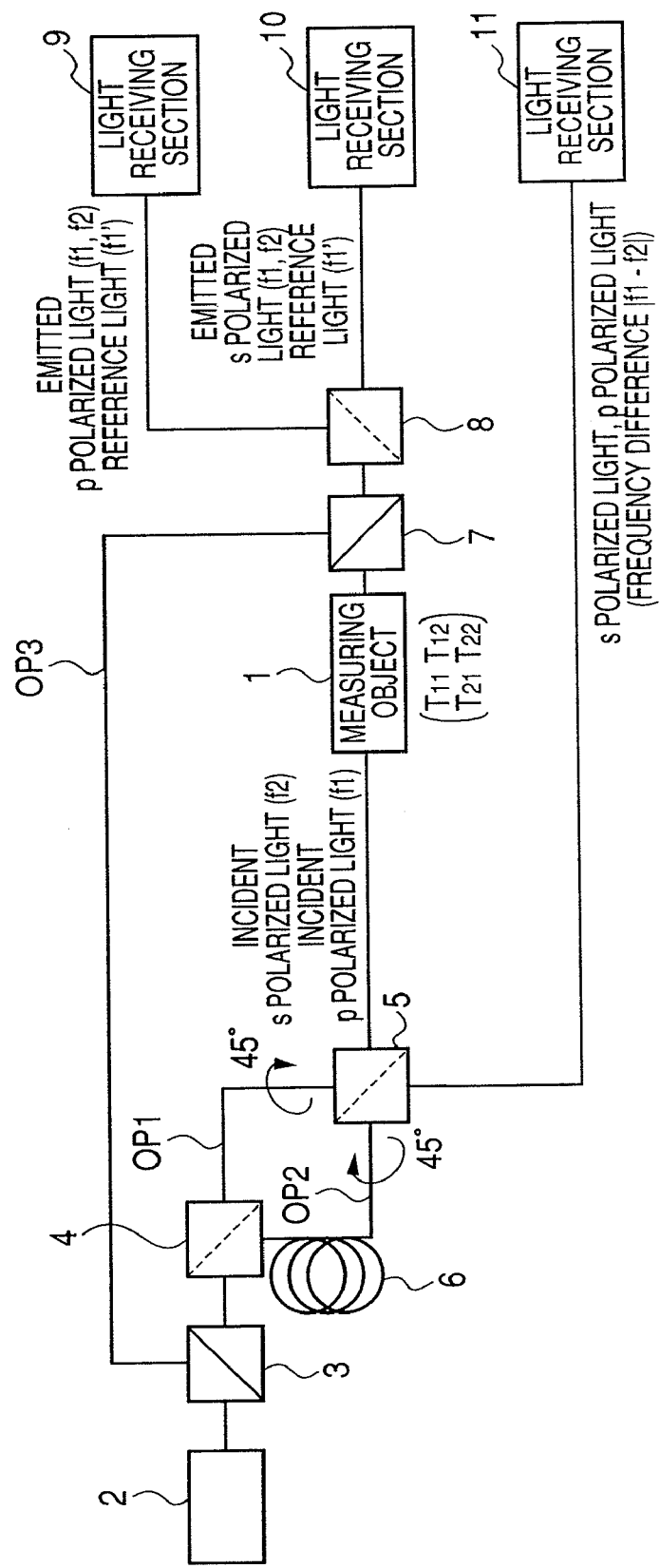
FIG. 15 is a diagram showing a configuration of an optical characteristic measuring apparatus of a related art.

FIG. 1 is a configuration diagram showing a first embodiment of the invention. Here, sections the same as those of FIG. 14, FIG. 15 are attached with the same notations and an explanation thereof will be omitted. In FIG. 1, a light source section 13 sweeps wavelengths (frequency sweep) of respective incident p polarized light (first input light) and incident s polarized light (second input light) of which frequencies (light frequencies) differ from each other and of which polarized states are perpendicular to each other so as to output the incident p polarized light and the incident s polarized light. Here, a frequency of incident p polarized light is designated by notation f1, and a frequency of incident polarized light is designated by notation f2 (f1≠f2).

An interference section 14 branches respective incident s polarized light, incident p polarized light from the light source section 13 and inputs one branched light to the measuring object 1 as signal light. Output light (signal light) from the measuring object 1 with regard to incident p polarized light, incident s polarized light is interfered with other branched light (reference light) to output a plurality of interference light. Further, interference lights outputted by the interference section 14 are (a) through (d) shown below.

(a) Incident p polarized light of reference light and emitted p polarized light of signal light.

(b) Incident s polarized light of reference light and emitted p polarized light of signal light.

(c) Incident p polarized light of reference light and emitted s polarized light of signal light.

(d) Incident s polarized light of reference light and emitted s polarized light of signal light.

Further, signal light and reference light at the interference section 14 are multiplexed naturally after having been transmitted by different optical paths. Here, when frequencies of reference light immediately before being multiplexed with signal light are designated by notations f1', f2', a frequency difference of first, second input light (|f1−f2|) outputted by the light source section 13 is set to be sufficiently larger than frequency differences (|f2−f2'|, |f1−f1'|) produced by an optical length difference of signal light and reference light.

For example, the frequency differences (|f2−f2'|, |f1−f1'|) are about 0 through 200 [kHz], and the frequency difference (|f1−f2|) by the light source section 13 is about several tens through several hundreds [MHz]. Naturally, optical lengths of signal light and reference light may be the same.

Light receiving sections 15 through 18 are provided for respective interference light outputted from the interference section 14 for receiving interference light and outputting signals in accordance with optical power of interference light.

Low-pass filters 19 through 22 are provided for the respective light receiving sections 15 through 18 for filtering signals outputted from the respective light receiving sections 15 through 18 and passing only signals of frequency components lower than the frequency difference (|f1−f2|) of incident s polarized light and incident p polarized light.

Operation of the apparatus will be explained.

The light source section 13 subjects incidents polarized light, incident p polarized light to wavelength sweep in a predetermined wavelength range to be outputted to the interference section 14.

The interference section 14 branches incident s polarized light, incident p polarized light and outputs one thereof to the measuring object 1 as signal light. Further, output light from the measuring object 1 returns to the interference section 14. That is, emitted s polarized light and emitted p polarized light with regard to incident s polarized light return, emitted s polarized light and emitted p polarized light with regard to incident p polarized light return. Further, the interference section 14 synthesizes emitted s polarized light, emitted p polarized light from the measuring object 1 and incident s polarized light, incident p polarized light of reference light to be interfered with each other.

Further, the interference section 14 outputs interference light of emitted s polarized light (frequencies f1, f2) and incident s polarized light (f2') to the light receiving section 15, outputs interference light of emitted s polarized light (frequencies f1, f2) and incident p polarized light (f1') to the light receiving section 16, outputs interference light of emitted p polarized light (frequencies f1, f2) and incident s polarized light (f2') to the light receiving section 17, outputs interference light of emitted p polarized light (frequencies f1, f2) and incident p polarized light (f1') to the light receiving section 18.

Further, the respective light receiving sections 15 through 18 output signals in accordance with optical power of interference light to the low-pass filters 19 through 22. Further, the low-pass filters 19 through 22 pass signals of low frequency components (for example, about DC through 200 [kHz]) of the interference signals outputted from the light receiving sections 15 through 18 to be outputted to calculating section, not illustrated, at a rear stage.

Specifically, the light receiving section 15 is inputted with emitted s polarized light (frequencies f1, f2), that is, signal light operated by $T_{11}$, $T_{12}$ of Jones matrix and reference light. Therefore, by filtering the interference signal from the light receiving section 15 by the low-pass filter 19, as the interference signal (incident s polarized light of frequency f2', emitted s polarized light of frequency f2) after having been filtered, only the interference signal operated only by $T_{11}$ of Jones matrix is extracted.

Similarly, as the interference signals after having been filtered by respective the low-pass filters 20 through 22, only the interference signals operated only by $T_{12}$, $T_{21}$, $T_{22}$ of Jones matrix are extracted.

Further, calculating section, not illustrated, at the rear stage obtains respective elements of Jones matrix from amplitudes and phases of the interference signals constituting output signals from the low-pass filters 19 through 22, and obtains an optical characteristic of the measuring object 1 from Jones matrix.

In this way, the interference section 14 outputs interference light of incident p polarized light and emitted s polarized light, interference light of polarized light of incident p polarized light and emitted p polarized light, interference light of incident s polarized light and emitted s polarized light, interference light of polarized light of incident s polarized light and emitted p polarized light, the interference signals are filtered by the low-pass filters 19 through 22. Thereby, the interference signals of low frequency components passing through the low-pass filter 19 through 22 are not effected with an influence of the frequency difference of incident s polarized light and incident p polarized light produced by nonlinearity of frequency sweep of the light source section 13. Therefore, even when the frequency difference of incident p polarized light and incident s polarized light is varied, the interference signal can accurately be measured. Further, only signals of the low frequency components are dealt with and therefore, circuit design of the low-pass filters 19 through 22, electric circuits at rear stages of the filters and the like is facilitated and the circuit configuration is simplified.

FIRST EXAMPLE OF INTERFERENCE SECTION

Figure 2:
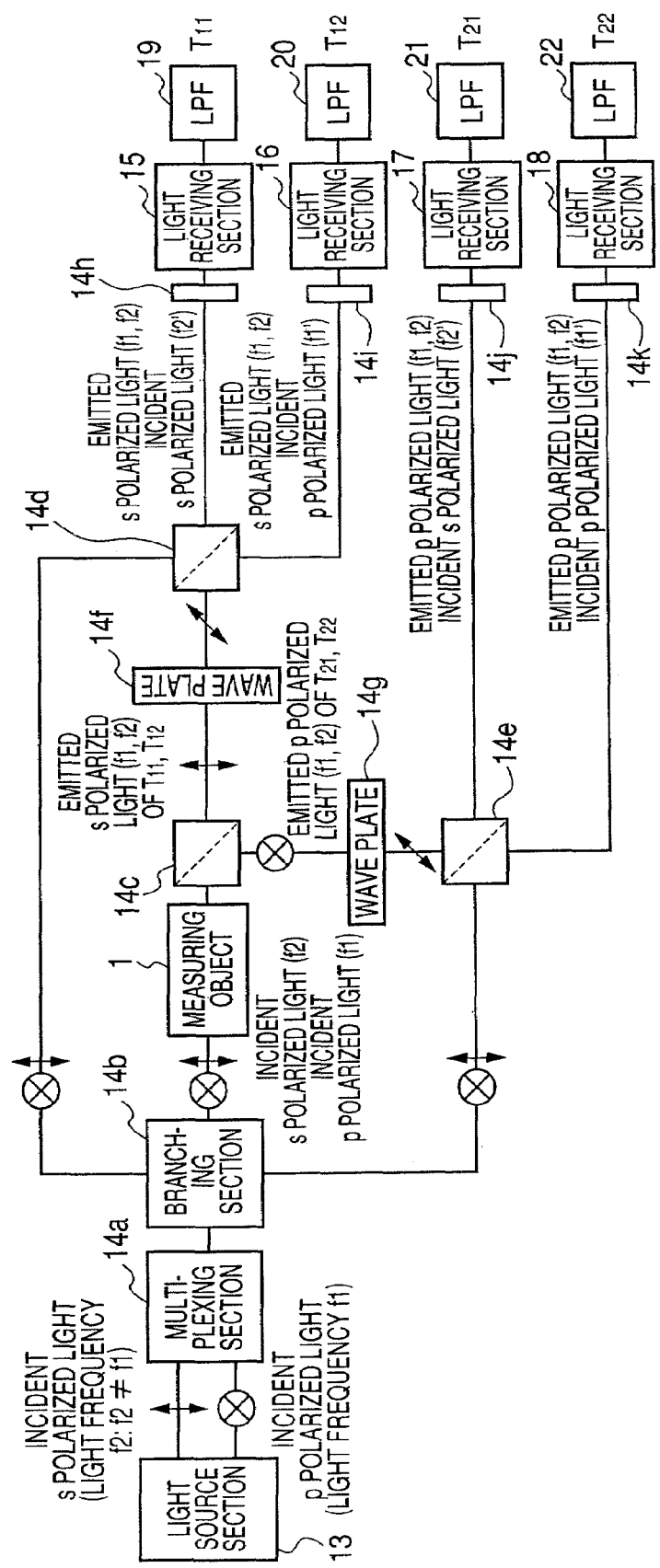
FIG. 2 is a configuration diagram showing a first example of an interference section provided in the apparatus shown in FIG. 1.

Next, FIG. 2 is a configuration diagram showing a first example of the interference section 14 in the apparatus shown in FIG. 1. Here, sections the same as those of FIG. 1 are attached with the same notations and an explanation thereof will be omitted. In FIG. 2, the interference section 14 includes a multiplexing section 14a, a branching section 14b, PBS 14c through 14e, wave plates 14f, 14g and polarizers 14h through 14k.

Further, the branching section 14b braches light without depending on a polarized state and is, for example, HM, a non-polarization beam splitter, an optical fiber coupler or the like. Further, the wave plates 14f, 14g are, for example, ½ wave plates or the like.

The multiplexing section 14a is, for example, a non-polarization beam splitter, HM, an optical fiber coupler or the like for multiplexing incident s polarized light, incident p polarized light from the light source section 13.

The input light branching section 14b branches light multiplexed by the multiplexing section 14a and inputs first branched light to the measuring object as signal light. Further, second, third branched light constitute reference light.

First PBS 14c branches output light from the measuring object 1 to emitted s polarized light, emitted p polarized light. The wave plate 14f is provided between PBS 14c and PBS 14d for inclining a polarization plane of emitted s polarized light by 45°. The wavelength plate 14g is provided between PBS 14c and PBS 14e for inclining a polarization plane of emitted p polarized light by 45°.

Second PBS 14d synthesizes second branched light (reference light) from the branching section 14c and emitted s polarized light from the wave plate 14f to be branched in two of lights of polarization planes of which are perpendicular to each other to be outputted to the light receiving sections 15, 16.

Third PBS 14e synthesizes third branched light (reference light) from the branching section 14c and emitted p polarized light from the wave plate 14g to be branched into two of light polarization planes of which are perpendicular to each other to be outputted to the light receiving sections 17, 18.

Respective the polarizers 14h through 14k are provided for respective branched light of PBS 14d, 14e, that is, provided between PBS 14d and the light receiving section 15, between PBS 14d and the light receiving section 16, between PBS 14e and the light receiving section 17, between PBS 14e and the light receiving section 18.

Operation of the apparatus will be explained.

The multiplexing section 14a synthesizes incident s polarized light (frequency f2), incident p polarized light (frequency f1) from the light source section 13. Further, the branching section 14b branches polarized light to signal light and reference light and outputs signal light to the measuring object 1. Here, emitted s polarized light (frequencies f1, f2), emitted p polarized light (frequencies f1, f2) are outputted from the measuring object 1, emitted s polarized light is operated by $T_{11}$, $T_{12}$, emitted p polarized light is operated by $T_{21}$, $T_{22}$.

Further, PBS 14c branches polarized light to emitted s polarized light, emitted p polarized light. A polarization plane of the branched emitted s polarized light is inclined by 45° by the wave plate 14f, thereafter, the branched emitted s polarized light is multiplexed with reference light (incident p polarized light (frequency f1'), incident s polarized light (frequency f2')) at PBS 14d and branched to light polarization planes of which are perpendicular to each other.

Thereby, one branched light of branched light outputted from PBS 14d is light constituted by multiplexing incident s polarized light (frequency f2') and emitted s polarized light (frequencies f1, f2) and other branched light thereof constitutes light multiplexed with incident p polarized light (frequency f1') and emitted s polarized light (frequencies f1,f2).

Further, polarization planes of light multiplexed and branched at PBS 14d are perpendicular to each other and therefore, light multiplexed and branched by PBS 14d are interfered with each other by inclining polarization planes by the polarizers 14h, 14i to be received by the light receiving sections 15, 16.

Similarly, a polarization plane of emitted p polarized light branched by PBS 14c is inclined by 45° by the wave plate 14g, thereafter, emitted p polarized light branched by PBS 14c is multiplexed with reference light (incident p polarized light (frequency f1'), incident s polarized light (frequency f2')) at PBS 14e, thereafter, branched to light polarization planes of which are perpendicular to each other.

Thereby, one branched light of branched light outputted from PBS 14e is light constituted by multiplexing incident s polarized light (frequency f2') and emitted p polarized light (frequencies f1, f2) and other branched light becomes light multiplexed with incident p polarized light (frequency f1') and emitted P polarized light (frequencies f1, f2).

Further, polarization planes of light multiplexed and branched by PBS 14e are perpendicular to each other and therefore, light multiplexed and branched by PBS 14e are interfered with each other by inclining the polarization planes by the polarizers 14j, 14k to be received by the light receiving sections 17, 18.

Further, output signals from the light receiving sections 15 through 18 are filtered respectively by the low-pass filters 19 through 22 and respective signals after having been filtered constitute interference signals operated only by $T_{11}$, $T_{12}$, $T_{21}$, $T_{22}$ of Jones matrix. Further, operation other than the above-described is similar to that of the apparatus shown in FIG. 1 and therefore, an explanation thereof will be omitted.

SECOND EXAMPLE OF INTERFERENCE SECTION

Figure 3:
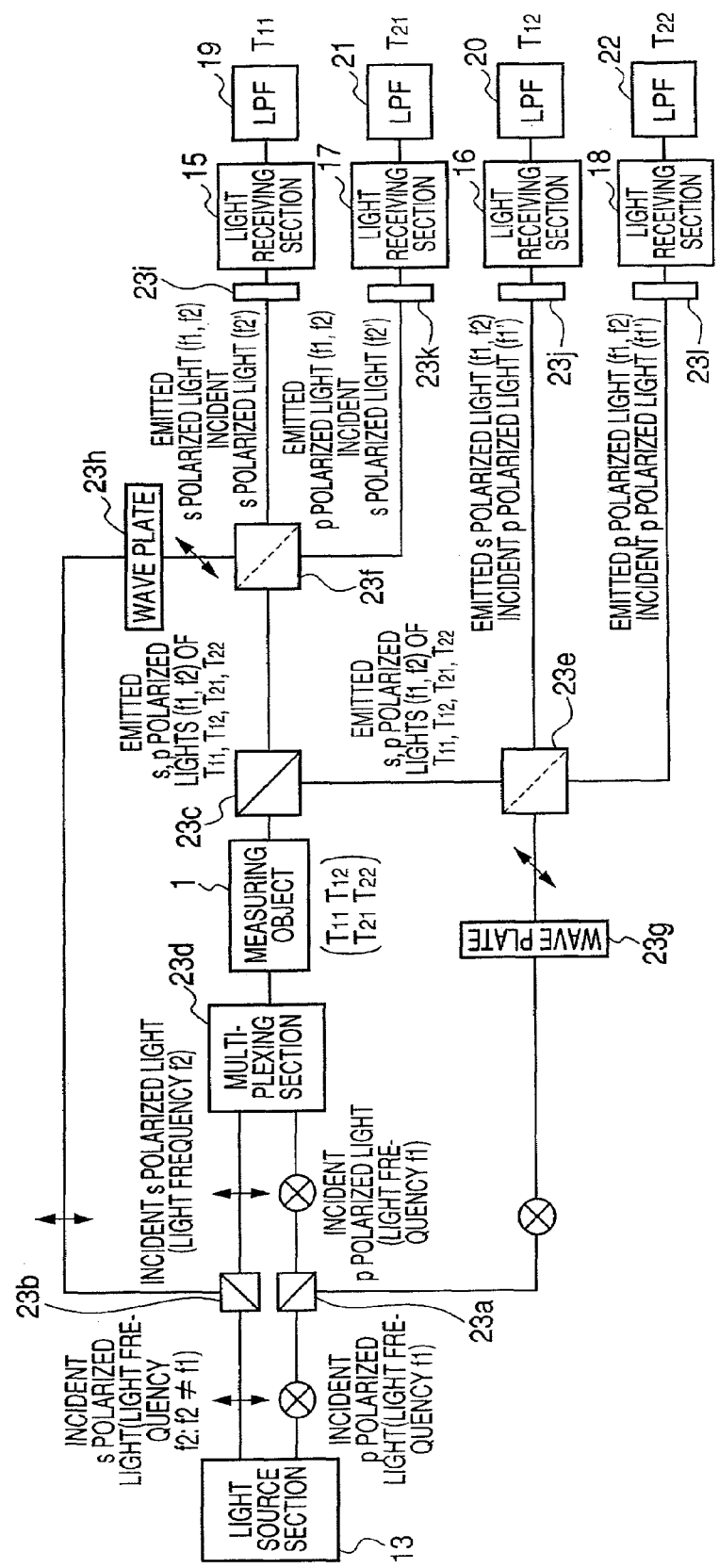
FIG. 3 is a configuration diagram showing a second example of the interference section provided in the apparatus shown in FIG. 1.

Next, FIG. 3 is a configuration diagram showing a second example of the interference section of the apparatus shown in FIG. 1. Here, sections the same as those of FIG. 1 are attached with the same notations and an explanation thereof will be omitted. In FIG. 3, an interference section 23 is provided in place of the interference section 14, the interference section 23 outputs interference light similar to that of the interference section 14 and includes branching sections 23a trough 23c, a multiplexing section 23d, PBS 23e, 23f, wave plates 23g, 23h, polarizers 23i through 23L.

Further, the branching sections 23a through 23c branch light without depending on a polarized state and are, for example, HM, non-polarization beam splitters, optical fiber couplers or the like. Further, the wave plates 23g, 23h are, for example, ½ plates or the like.

The first input light branching section 23a branches incident p polarized light (frequency f1) from the light source section 13 in two, outputs one thereof to the multiplexing section 23d as signal light and outputs other thereof to the wave plate 23g as reference light.

The second input light branching section 23b branches incidents polarized light (frequency f2) from the light source section 13 in two, outputs one thereof to the multiplexing section 13d as signal light and outputs other thereof to the wave plate 23h as reference light.

The multiplexing section 23d is, for example, PBS, a non-polarization beam splitter, HM, an optical fiber coupler or the like for multiplexing signal light from the branching section 23a, 23b to be outputted to the measuring object 1.

The output light branching section 23c branches output light (signal light) from the measuring object 1 in two, outputs one thereof to PBS 23e and outputs other thereof to PBS 23f.

The wave plate 23g is provided between the branching section 23a and PBS 23e and inclines a polarization plane of incident p polarized light of reference light by 45°.

First PBS 23e synthesizes one branched light (signal light) from the branching section 23c and incident p polarized light of reference light from the wave plate 23g to be branched in two of light polarization planes of which are perpendicular to each other to be outputted to the light receiving sections 16, 18.

Second PBS 23f synthesizes other branched light (signal light) from the branching section 23c and incident s polarized light of reference light from the wave plate 23h to be branched in two of light polarization planes of which are perpendicular to each other to be outputted to the light receiving sections 15, 17.

Respective the polarizers 23i through 23L are provided for respective branched light of PBS 23e, 23f, that is, provided between PBS 23f and the light receiving section 15, between PBS 23e and the light receiving section 16, between PBS 23f and the light receiving section 17, between PBS 23e and the light receiving section 18.

Operation of the apparatus will be explained.

The branching section 23a braches incident p polarized light (frequency f1) from the light source section 13 in two, outputs one thereof to the multiplexing section 23d as signal light and outputs other thereof to the wave plate 23g as reference light. Further, the branching section 23b branches incidents polarized light (frequency f2) from the light source section 13 in two, outputs one thereof to the multiplexing section 23d as signal light and outputs other thereof to the wave plate 23h as reference light. Further, respective the wave plates 23g, 23h incline polarization planes of reference light by 45°.

Further, the multiplexing section 23d synthesizes signal light from the branching sections 23a, 23b to be outputted to the measuring object 1. Further, when the multiplexed section 23d synthesizes light by using PBS, the multiplexing section 23d can synthesize light more efficiently than an optical element (for example, HM, non-polarization beam splitter, optical fiber coupler or the like) for multiplexing and branching light without depending on a polarized state.

Further, the branching section 23c branches emitted s polarized light (frequencies f1, f2), emitted p polarized light (frequencies f1, f2) outputted from the measuring object 1, outputs one thereof to PBS 23e and outputs other thereof to PBS 23f. Naturally, emitted s polarized light is operated by $T_{11}$, $T_{12}$, emitted p polarized light is operated by $T_{21}$, $T_{22}$.

Further, PBS 23e synthesizes reference light (incident p polarized light (frequency f1')) from the wave plate 23g and signal light (emitted s polarized light (frequencies f1, f2), emitted p polarized light (frequencies f1, f2)) to be thereafter branched into light polarization planes of which are perpendicular to each other, outputs one thereof to the polarizer 23j and output other thereof to the polarizer 23L.

Thereby, one branched light of branched light outputted from PBS 23e is light constituted by multiplexing incident p polarized light (frequency f1') and emitted s polarized light (frequencies f1, f2), and other branched light becomes light multiplexed with incident p polarized light (frequency f1') and emitted p polarized light (frequencies f1, f2).

Further, polarization planes of light multiplexed and branched by PBS 23e are perpendicular to each other and therefore, light multiplexed and branched by PBS 23e are interfered with each other by inclining polarization planes by the polarizers 23j, 23l to be received by the light receiving sections 16, 18.

Similarly, PBS 23f synthesizes reference light (incident s polarized light (frequency f2')) from the wave plate 23h and signal light (emitted s polarized light (frequencies f1, f2), emitted polarized light (frequencies f1, f2)) to be thereafter branched to light polarization planes of which are perpendicular to each other, outputs one thereof to the polarizer 23i and outputs other thereof to the polarizer 23k.

Thereby, one branched light of branch light outputted from PBS 23f is light constituted by multiplexing incident s polarized light (frequency f2') and emitted s polarized light (frequencies f1, f2), and other branched light becomes light multiplexed with incident s polarized light (frequency f2') and emitted p polarized light (frequencies f1, f2).

Further, polarization planes of light multiplexed and branched by PBS 23f are perpendicular to each other and therefore, light multiplexed and branched by PBS 23f are interfered with each other by inclining polarization planes by the polarizers 23i, 23k to be received by the light receiving sections 15, 17.

Output signals from the light receiving sections 15 through 18 are filtered by respective the low-pass filters 19 through 22, respective signals after having been filtered become interference signals operated only by $T_{11}$, $T_{12}$, $T_{21}$, $T_{22}$ of Jones matrix. Further, operation other than the above-described is similar to that of the apparatus shown in FIG. 1 and therefore, an explanation thereof will be omitted.

THIRD EXAMPLE OF INTERFERENCE SECTION

Figure 4:
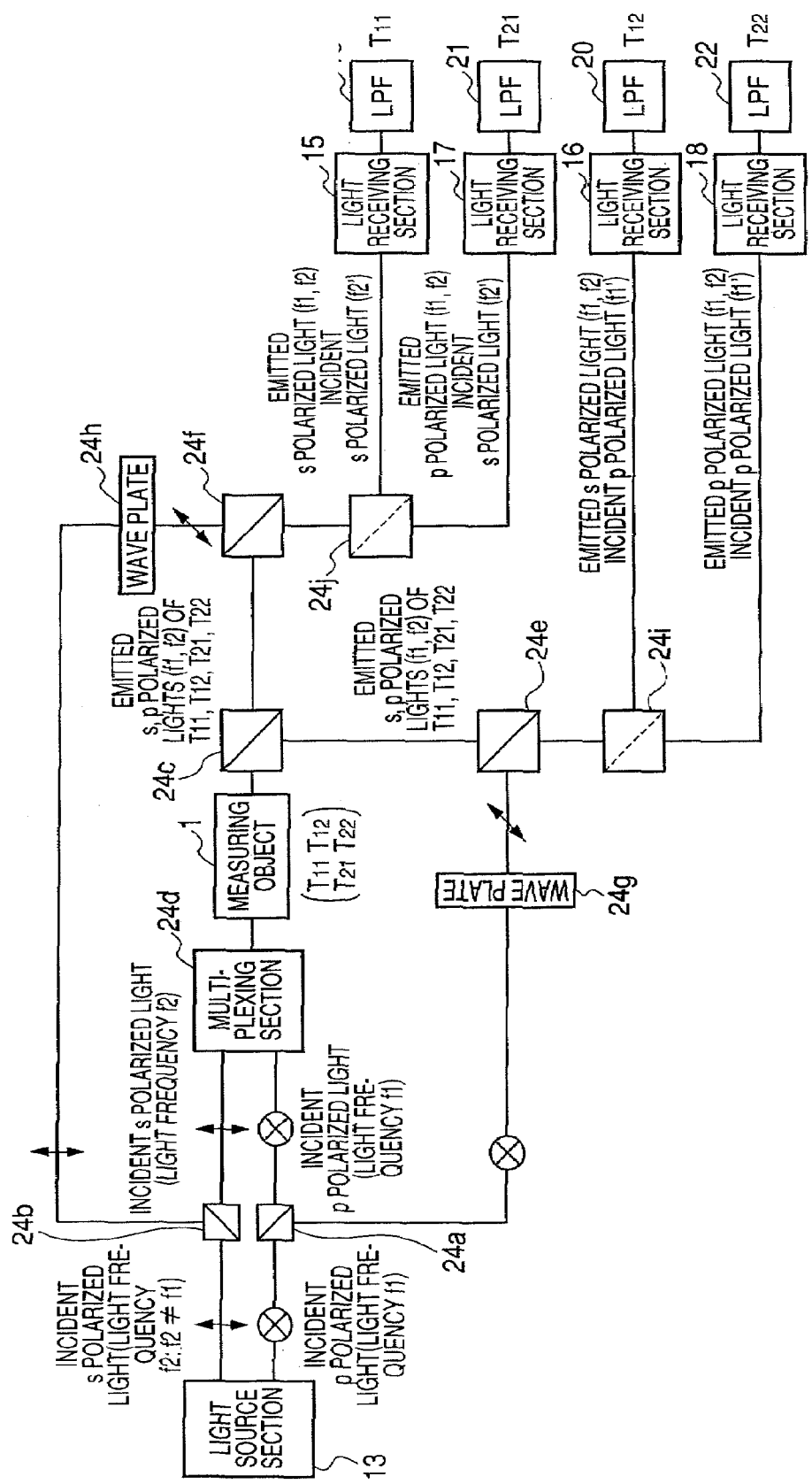
FIG. 4 is a configuration diagram showing a third example of the interference section provided in the apparatus shown in FIG. 1.

Next, FIG. 4 is a configuration diagram showing a third example of the interference section of the apparatus shown in FIG. 1. Here, sections the same as those of FIG. 1 are attached with the same notations and an explanation thereof will be omitted. In FIG. 4, an interference section 24 is provided in place of the interference section 14, the interference section 24 outputs interference light similar to that of the interference section 14 and includes branching sections 24a through 24c, multiplexing sections 24d through 24f, wave plates 24g, 24h, and PBS 24i, 24j.

Further, the branching sections 24a through 24c branch light without depending on a polarized state, and are, for example, HM, non-polarization beam splitters, optical fiber couplers or the like. The multiplexing sections 24e, 24f synthesize light without depending on a polarized state, and are, for example, HM, non-polarization beam splitters, optical fiber couplers or the like. The wave plates 24g, 24h are for example, ½ wave plates.

The first input light branching section 24a branches incident p polarized light (frequency f1) from the light source section 13 in two, outputs one thereof to the multiplexing section 24d as signal light and outputs other thereof to the wave plate 24g as reference light.

The second input light branching section 24b branches incident s polarized light (frequency f2) from the light source section 13 in two, outputs one thereof to the multiplexing section 24d as signal light and outputs other thereof to the wave plate 24h as reference light.

The multiplexing section 24d is, for example, PBS, a non-polarization beam splitter, HM, an optical fiber coupler or the like, synthesizes signal light from the branching sections 24a, 24b to be outputted to the measuring object 1. The branching section 24c branches output light (signal light) from the measuring object 1 in two, outputs one thereof to the multiplexing section 24e and outputs other thereof to the multiplexing section 24f.

The wave plate 24g is provided between the branching section 24a and the multiplexing section 24e for inclining a polarization plane of incident p polarized light of reference light by 45°. The wave plate 24h is provided between the branching section 24b and the multiplexing section 24f for inclining a polarization plane of emitted s polarized light of reference light by 45°.

The first output light multiplexing section 24e synthesizes and interferes one branched light (signal light) from the branching section 24c and incident p polarized light of reference light from the wave plate 24g.

The second output light multiplexing section 24f synthesizes and interferes other branched light (signal light) from the branching section 24c and incident s polarized light of reference light from the wave plate 24h.

The first PBS 24i branches multiplexed light from the multiplexing section 24e in two of light polarization planes of which are perpendicular to each other to be outputted to the light receiving sections 15, 18. The second PBS 24j branches multiplexed light from the multiplexing section 24f in two of light polarization planes of which are perpendicular to each other to be outputted to the light receiving sections 15, 17.

Operation of the apparatus will be explained.

The branching section 24a branches incident p polarized light (frequency f1) from the light source section 13 in two, outputs one thereof to the multiplexing section 14d as signal light and outputs other thereof to the wave plate 24g as reference light. Further, the branching section 24b branches incident s polarized light (frequency f2) from the light source section 13 in two, outputs one thereof to the multiplexing section 24d as signal light, and outputs other thereof to the wave plate 24h as reference light. Further, respective the wave plates 24g, 24h incline polarization planes of reference light by 45°.

Further, the multiplexing section 24d synthesizes signal light from the branching sections 24a, 24b to be outputted to the measuring object 1. Further, when the multiplexing section 24d synthesizes light by using PBS, light can be multiplexed more efficiently than an optical element (for example, HM, non-polarization beam splitter, optical fiber coupler or the like) for multiplexing and branching light without depending on a polarized state.

Further, the branching section 24c branches emitted s polarized light (frequencies f1, f2), emitted p polarized light (frequencies f1, f2) outputted from the measuring object 1 in two, outputs one thereof to the multiplexing section 24e and outputs other thereof to the multiplexing section 24f. Naturally, emitted, s polarized light is operated by $T_{11}$, $T_{12}$, and emitted p polarized light is operated by $T_{21}$, $T_{22}$.

Further, the multiplexing section 24e synthesizes and interferes reference light (incident p polarized light (frequency f1')) from the wave plate 24g and signal light (emitted s polarized light (frequencies f1, f2)), emitted p polarized light (frequencies f1, f2)). Further, PBS 24i branches interference light multiplexed by the multiplexing section 24e to light polarization planes of which are perpendicular to each other, outputs one thereof to the light receiving section 16 and outputs other thereof to the light receiving section 18.

Thereby, one branched light of branched light outputted from PBS 24i is interference light constituted by multiplexing incident p polarized light (frequency f1') and emitted s polarized light (frequencies f1, f2), and other branched light becomes interference light multiplexed with incident p polarized light (frequency f1') and emitted p polarized light (frequencies f1, f2).

Further, respective branched light branched by PBS 24i are received by the light receiving sections 16, 18.

Similarly, the multiplexing section 24f synthesizes and interferes reference light (incident s polarized light (frequency f2')) from the wave plate 24h and signal light (emitted s polarized light (frequencies f1, f2), emitted p polarized light (frequencies f1, f2)). Further, PBS 24j branches interference light multiplexed by the multiplexing section 23f to light polarization planes of which are perpendicular to each other, outputs one thereof to the light receiving section 15 and outputs other thereof to the light receiving section 17.

Thereby, one branched light of branched light outputted from PBS 24j is light constituted by multiplexing incident s polarized light (frequency f2') and emitted s polarized light (frequencies f1, f2), and other branched light becomes interference light multiplexed with incident s polarized light (frequency f2') and emitted p polarized light (frequencies f1, f2).

Further, respective branched light branched by PBS 24j are received by the light receiving sections 15, 17.

Further, output signals from the light receiving sections 15 through 18 are filtered by respective the low-pass filters 19 through 22, and respective signals after having been filtered become interference signals operated by only $T_{11}$, $T_{12}$, $T_{21}$, $T_{22}$ of Jones matrix. Further, operation other than the above-described is similar to that of the apparatus shown in FIG. 1 and therefore, an explanation thereof will be omitted.

FOURTH EXAMPLE OF INTERFERENCE SECTION

Figure 5:
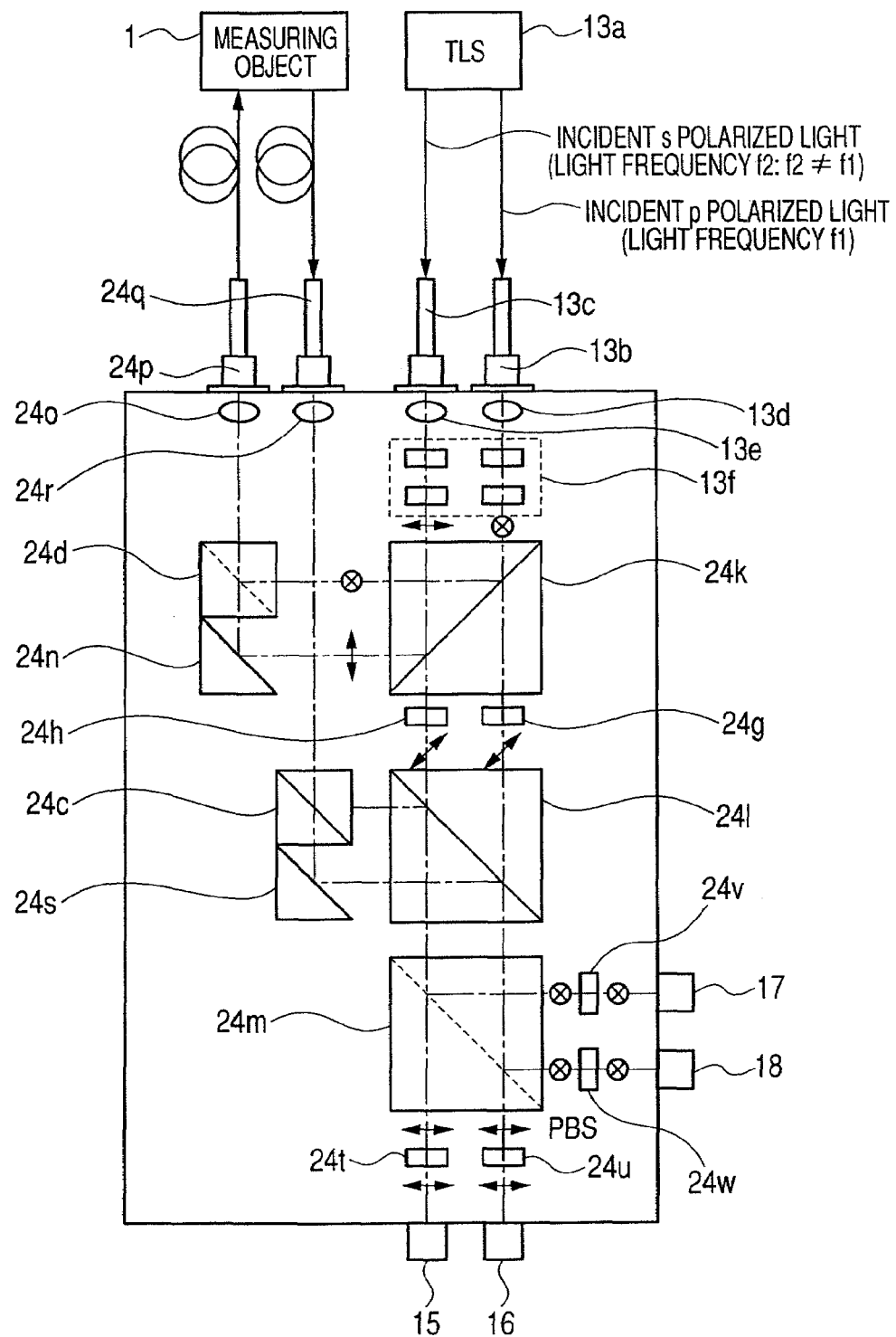
FIG. 5 is a configuration diagram showing a fourth example of the interference section provided in the apparatus shown in FIG. 1.

Next, FIG. 5 is a configuration diagram showing a fourth example of the interference section in the apparatus shown in FIG. 1. Here, sections the same as those of FIG. 1, FIG. 4 are attached with the same notations and an explanation thereof will be omitted. In FIG. 5, HM 24k is constituted by commonly integrating the branching sections 24a, 24b, HM 24l is constituted by commonly integrating the multiplexing sections 24e, 24f, PBS 24m is constituted by commonly integrating PBS 24i, 24j.

The light source section 14 includes a wavelength variable light source 13a, optical fibers 13b, 13c, lenses (collimator section) 13d, 13e, a polarized wave controller 13f. The wavelength variable light source 13a subjects respective light having different frequencies to wavelength sweep to be outputted. The optical fiber 13b transmits light of the frequency f1 from the light source section 13a. The optical fiber 13c transmits light of the frequency f2 from the light source section 13a. Further, the optical fibers 13b, 13c are installed such that optical axes of emitted light become in parallel with each other.

Respective the lenses 13d, 13e make light emitted from the optical fibers 13b, 13c parallel light. The polarized wave controller 13f, for example, arranged in series with ¼ wave plates, ½ wave plates is provided to optical paths, converts light from the lens 13d into incident p polarized light (first input light) and converts light from the lens 13e into incident S polarized light (second input light) to be outputted to the interference section 24.

A mirror 24n reflects incident s polarized light from HM 24k to PBS 24d.

A lens (light converging section) 24o makes light multiplexed by PBS 24d incident on an optical fiber 24p. The optical fiber 24p transmits incident p polarized light, incident s polarized light from the interference section 24 to the measuring object 1.

An optical fiber 24q transmits emitted p polarized light, emitted s polarized light from the measuring object 1. A lens (collimator section) 24r makes emitted p polarized light, emitted s polarized light from the optical fiber 24q parallel light to be outputted to HM 24c. A mirror 24s reflects one branched light from HM 24c to HM 24l.

Respective polarizers 24t through 24w are provided between PBS 24m and the light receiving section 16, between PBS 24m and the light receiving section 17, between PBS 24m and the light receiving section 18, between PBS 24m and the light receiving section 19 to pass light of only a predetermined polarization plane.

Operation of the apparatus will be explained.

Respective light of the frequencies f1, f2 from the wavelength variable light source 13a are transmitted to the polarized wave controller 13f by the fibers 13b, 13c, the lenses 13d, 13e. Further, the polarized wave controller 13f converts respective polarized light states of light of the frequencies f1, f2 to be outputted to HM 24k of the interference section 24 as incident p polarized light, incident s polarized light.

Further, HM 24k branches incident s polarized light, incident p polarized light to signal light and reference light. Branched incident s polarized light (signal light) is reflected by the mirror 24n, multiplexed with incident p polarized light (signal light) by PBS 24d, and is inputted to the measuring object 1 by way of the lens 24o, the optical fiber 24p.

Further, emitted p polarized light, emitted s polarized light from the measuring object 1 are inputted to HM 24c by way of the optical fiber 24q, the lens 24r.

Further, HM 24c branches emitted p polarized light, emitted s polarized light to two, one branched light is reflected by the mirror 24s and is incident on HM 24l, other branched light is incident on HM 24l.

Thereby, HM 24l synthesizes reference light (incident p polarized light (frequency f1')) from the wave plate 24g, signal light (emitted s polarized light (frequencies f1, f2), emitted p polarized light (frequencies f1, f2)) and synthesizes reference light (incident s polarized light (frequency f2')) from the wave plate 24h, signal light (emitted S polarized light (frequencies f1, f2), emitted p polarized light (frequencies f1, f2)).

Further, PBS 24m branches interference light multiplexed by the multiplexing section 24l to light polarization planes of which are perpendicular to each other to be outputted to the light receiving sections 15 through 18 by way of the polarizers 24t to 24w. Here, different from the polarizers shown in FIG. 2, FIG. 3, the polarizers 24t through 24w pass light of only a predetermined polarization plane. For example, the polarizers 24t, 24u pass light of a polarization plane the same as that of incident s polarized light from the polarized wave controller 13f, the polarizers 24b, 24w pass light of a polarization plane the same as that of incident p polarized light from the polarized wave controller 13f. That is, this is because it is difficult for PBS 24m to completely branch inputted light to light polarization plane of which are perpendicular to each other and light which has not been branched is removed.

Further, the light receiving sections 15 through 18 receive interference signals to be outputted to the low-pass filters 19 through 22, not illustrated, at a rear stage. Further, outputted signals from the light receiving sections 15 through 18 are filtered by respective the low-pass filters 19 through 22. Thereby, respective signals after having been filtered become interference signals operated only by $T_{11}$, $T_{12}$, $T_{21}$, $T_{22}$ of Jones matrix. Further, operation other than the above-described is similar to that of the apparatus shown in FIG. 1 and therefore, an explanation thereof will be omitted.

In this way, the polarizers 24t through 24w pass only light of a predetermined polarization plane to be outputted to the light receiving sections 15 through 18 and therefore, noise of the interference signals can be reduced.

Further, the branching sections 24a, 24b are made common, the multiplexing sections 24e, 24f are made common, PBS 24i, 24j are made common and therefore, a number of parts is reduced to achieve small-sized formation, facilitating alignment, a reduction in cost.

Further, by constituting the interference section by an interferometer of a spatial light type, an optical system can be downsized and is made to be strong at vibration.

Further, the invention is not limited to the first embodiment and the first to fourth examples of the interference section but may be as shown below.

Although there is shown a configuration in which the light source section 13 outputs p polarized light, s polarized light which are linearly polarized light and polarization planes of which are perpendicular to each other as first, second input light in the apparatus shown in FIG. 1 through FIG. 5, first, second input light may be constituted by polarized light polarized states of which are perpendicular to each other (for example, circularly polarized light, elliptically polarized light).

Although there is shown a configuration in which output light (emitted p polarized light, emitted s polarized light) for interfering with reference light are respectively branched to linearly polarized light in the apparatus shown in FIG. 1 through FIG. 5, output light including frequencies f1, f2 may be branched to the light of a first polarized state, a second polarized state, respective which may interfere with reference light. Further, first, second polarized states are perpendicular to each other.

Although there is shown a configuration of providing the wave plates 14f, 14g, 23g, 23h, 24g, 24h in the apparatus shown in FIG. 2 through FIG. 5, the wave plates may not be provided when a polarization plane of light inputted to PBS at a rear stage is inclined to an optical axis of PBS.

Although there is shown a configuration of using an interferometer of Mach-Zender type for the interference sections 14, 23, 24 in the apparatus shown in FIG. 2 through FIG. 5, any two light flux interferometer may be used.

In the apparatus shown in FIG. 3, similar to the apparatus shown in FIG. 5, the branching sections 23a, 23b may be made common, PBS 23e, 23f may be made common.

Although there is shown a configuration of providing the polarized wave controller 13f between HM 24k and the lenses 13d, 13e in the apparatus shown in FIG. 5, for example, the polarized wave controllers 13f may be provided at middles of the optical fibers 13b, 13c, light emitted from the optical fibers 13b, 13c may already become incident p polarized light, incident s polarized light.

Although there is shown a configuration of providing the polarizers 24t through 24w in the apparatus shown in FIG. 5, the polarizers 24t through 24w may not be provided.

Second Embodiment

Figure 6:
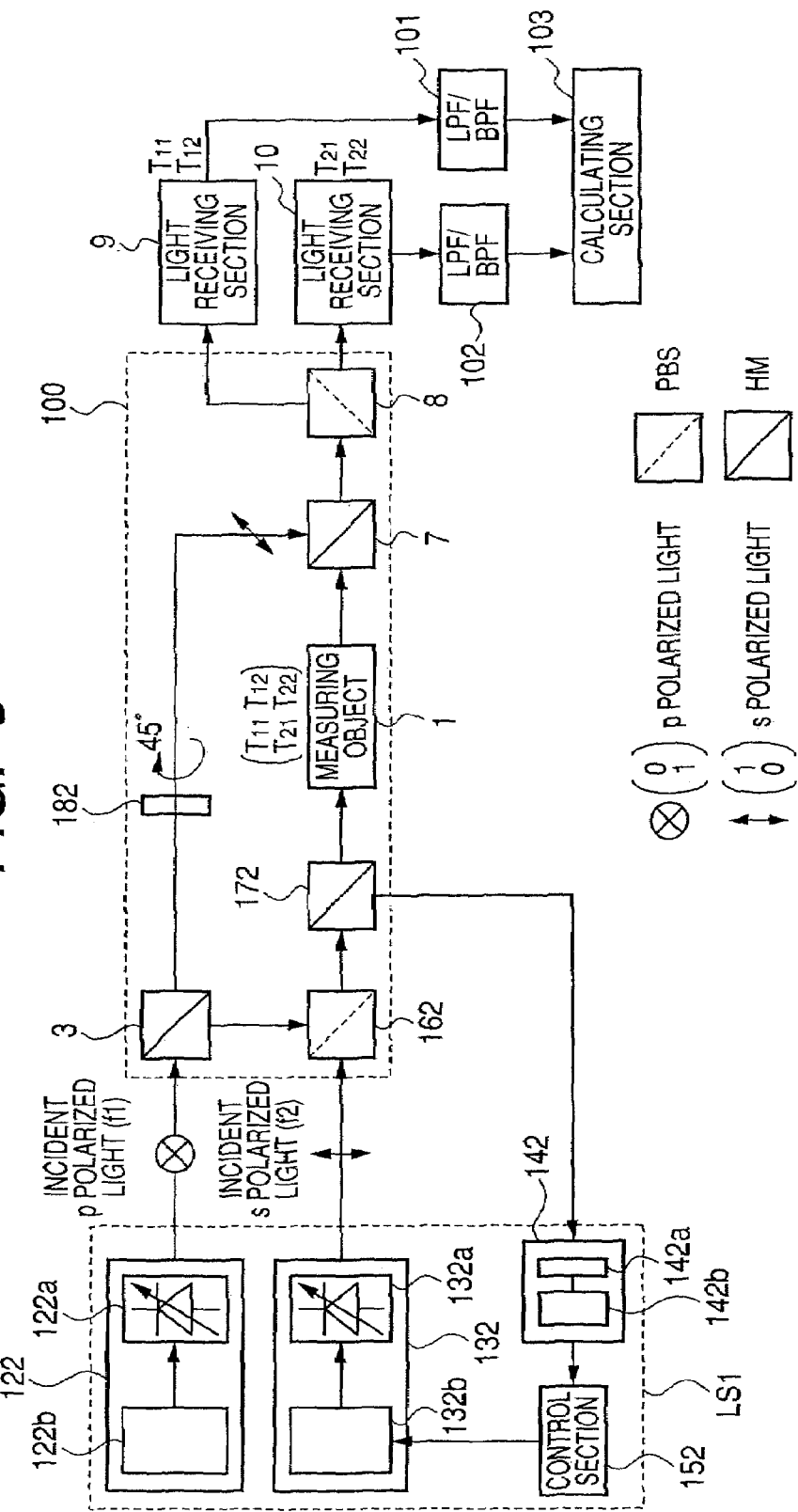
FIG. 6 is a configuration diagram showing a second embodiment of the invention.
Figure 16:
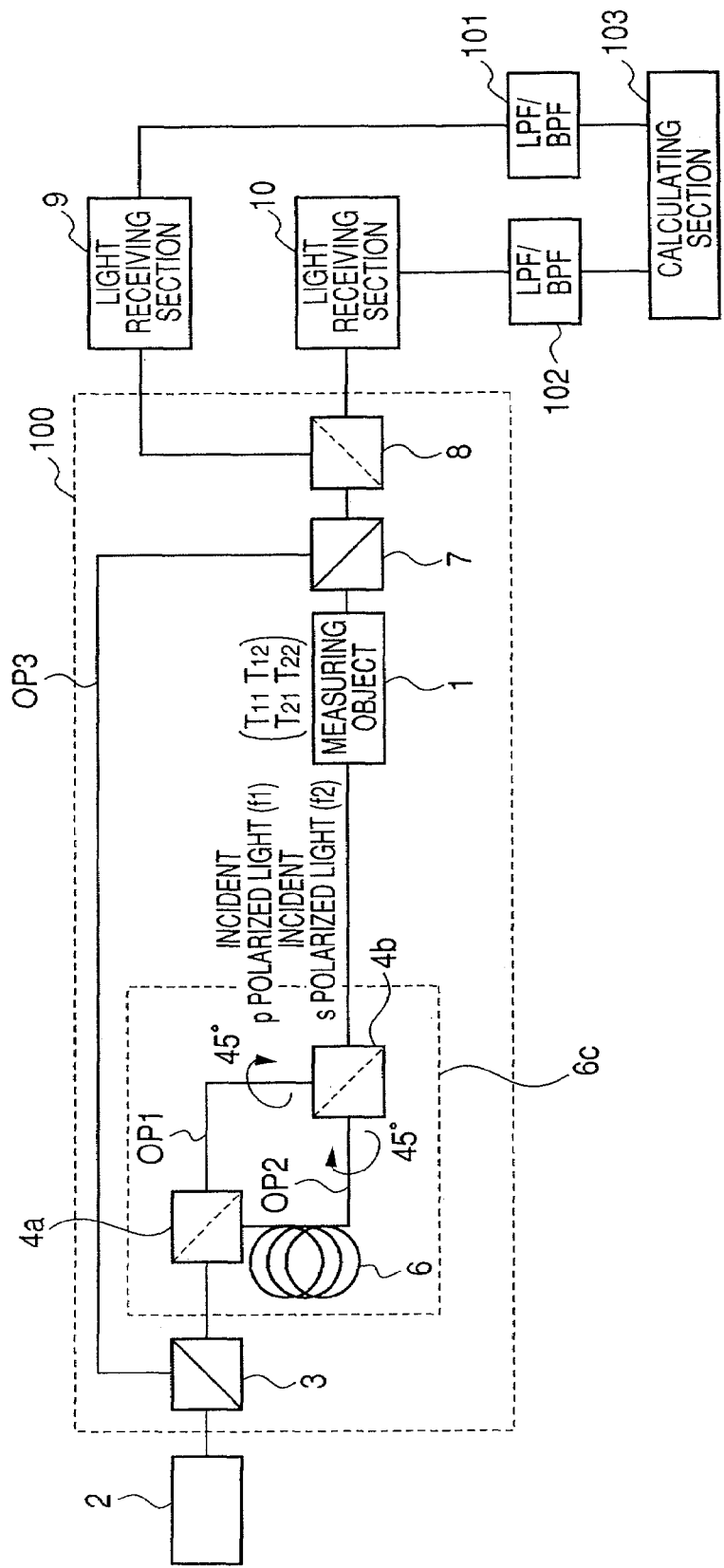
FIG. 16 is a diagram showing a configuration of an optical characteristic of a measuring apparatus of a related art.

FIG. 6 is a configuration diagram showing a second embodiment of the invention. Here, sections the same as those of FIG. 14, FIG. 16 are attached with the same notations and an explanation thereof will be omitted. In FIG. 6, a light source section LS1 is provided in place of the wavelength variable light source 2. The light source section LS1 includes a first wavelength variable light source 122, a second wavelength variable light source 132, a detecting section 142, a control section 152, and outputs first, second input light having a predetermined frequency difference therebetween to an interference section 100.

The first wavelength variable light source 122 on a master side includes an LD light source 122a, a wavelength sweep circuit 122b for subjecting p polarized light (first input light) to wavelength sweep to be outputted to the interference section 100. The LD light source 122a subjects a measuring wavelength range continuously to wavelength sweep to output laser light by an instruction from the wavelength sweep circuit 122b.

The second wavelength variable light source 132 on a slave side includes an LD light source 132a, a wavelength sweep circuit 132b for subjecting s polarized light (second input light) to wavelength sweep to be outputted to the interference section 100. The LD light source 132a subjects a measuring wavelength range continuously to wavelength sweep to output laser light by an instruction from the wavelength sweep circuit 132b.

The LD light sources 122a, 132a for outputting laser light are surface emitting lasers forming resonators by movable mirrors (reflecting layers) formed by a semiconductor micromachining technology. Further, the surface emitting laser (VCSEL: Vertical-Cavity Surface-Emitting Laser) is constituted by a structure of interposing a semiconductor layer by a reflecting layer formed by multilayered films or the like. Further, the semiconductor layer is formed by multilayers including an active layer and a spacer layer (referred to also as clad layer) for interposing the active layer (refer to, for example, "Connie J. Chang-Hasnain, "tunable VCSEL", by IEEE JOURNAL ON SELECTED TOPICS IN QUANTUM ELECTRONICS, Vol. 6, No. 6, NOVEMBER/DECEMBER 2000, pp 978-987" or "D. Vakhashoori, P. D. Wang, M. Azimi, K. J. Knopp, M. Jiang, "MEMs-Tunable Vertical-Cavity Surface-Emitting Lasers", Proc. of OFC2001, TuJ1-1 through TuJ1-3" or the like.

The detecting section 142 includes a polarizer 142a, a light receiving section 142b, and detects a frequency difference of s polarized light, p polarized light outputted by the wavelength variable light sources 122, 132. The polarizer 142a rotates polarization planes of s polarized light, p polarized light to be interfered with each other. The light receiving section 142b receives interference light of S polarized light, p polarized light and outputs a signal in accordance with received optical power.

The control section 152 controls a wavelength sweep speed of the wavelength variable light source 132 based on the frequency difference detected by the detecting section 142 and controls constant the frequency difference of laser light outputted by the plane variable light sources 122, 132.

At the interference section 100, the polarized light delay section 6c is removed and PBS 162, HM 172 are provided between HM 3 and the measuring object 1. Further, a polarization plane rotating section 182 is provided between HM 3 and HM 7 (optical path on reference light side).

PBS 162 multiplexes one branched light from HM 3 and s polarized light from the wavelength variable light source 132. HM 172 branches light from PBS 162 and outputs one thereof to the measuring object 1 and outputs other thereof to the detecting section 142.

The polarization plane rotating section 182 is a ½ wave plate, when, for example, an interval between HM 3 and HM 7 is constituted by spatial light, an incident end and an emitting end thereof are installed to be inclined by 45° when the interval is constituted by a polarized wave holding optical fiber for rotating a polarization plane of other branched light from HM 3 by 45° relative to an optical axis of PBS 8.

Operation of the apparatus will be explained.

Respective the wavelength sweep circuits 122b, 132b of the wavelength variable light sources 122, 132 make the LD light sources 122a, 132a output laser light of frequencies f1, f2 to be subjected to wavelength sweep by a predetermined wavelength sweep speed. Further, the wavelength sweep circuits 122b, 132b read set values (start wavelength/finish wavelength, sweep speed and the like of wavelength sweep) from a memory, not illustrated, and issue an instruction to the LD light sources 122a, 132a in accordance with the set values. Further, a set value of a frequency difference (|f1−f2|) of the wavelength variable light sources 122, 132 in starting to output laser light is set to, for example, 50 [MHz].

Further, a polarized wave controller, not illustrated, converts polarized states of laser light respectively from the wavelength variable light sources 122, 132 top polarized light, S polarized light to output to the interference section 100 as incident p polarized light, incident s polarized light. Naturally, when laser light outputted from the wavelength variable light sources 122, 132 are constituted by p polarized light, s polarized light, the polarized wave controller is not needed.

Further, HM 3 of the interference section 100 branches incident p polarized light, outputs one thereof to PBS 162 as signal light and outputs other thereof to the polarization plane rotating section 182 as reference light. Further, the polarization plane rotating section 182 inclines a polarization plane of reference light by 45° such that optical power is uniformly branched at PBS 8 at a rear stage.

Successively, an explanation will be given of a side of one branched light (signal light) from HM 3. PBS 162 multiplexes incident s polarized light and incident p polarized light from HM 3. Naturally, since multiplexed by PBS 162, incident s polarized light and incident p polarized light become linearly polarized light perpendicular to each other. Further, HM 172 branches multiplexed light from PBS 162 to output one thereof to the measuring object 1 and outputs other thereof to the detecting section 142.

Further, in order to make incident p polarized light and incident s polarized light interfere with each other, the polarizer 142a of the detecting section 142 inclines a polarization plane to thereby make incident p polarized light and incident s polarized light interfere with each other to be outputted to the light receiving section 142b. Further, the light receiving section 142b outputs a signal in accordance with optical power of interference light, the detecting section 142 obtains a frequency of an interference signal (beat signal) from the light receiving section 142b and detects a frequency difference of incident p polarized light and incident s polarized light to be outputted to the control section 152.

Further, the control section 152 controls the wavelength sweep circuit 132b of the wavelength variable light source 132 based on the frequency difference detected by the detecting section 142 to thereby make the frequency difference of laser light outputted by the wavelength variable light sources 122, 132 constant (50 [MHz]). Further, the control section 152 reads the value of the frequency difference previously from a memory, not illustrated.

Further, operation thereafter of multiplexing reference light from the polarization plane rotating section 182 and output light from the measuring object 1 by HM7 to be outputted to PBS 8 to be received by the light receiving sections 9, 10 is similar to that of the apparatus shown in FIG. 16.

That is, interference light branched by PBS 8 and inputted to the light receiving section 9 is by output light combined with $T_{11}$, $T_{12}$ of Jones matrix and reference light. Further, interference light inputted to the light receiving section 10 is constituted by output light combined with $T_{21}$, $T_{22}$ of Jones matrix and the reference light.

Further, an interference signal influenced by $T_{11}$ is incident s polarized light (frequency f2) outputted from the wavelength variable light source 132 on the slave side and passed through the measuring object 1. That is, a frequency thereof differs from that of reference light (frequency f1') from the wavelength variable light source 122 on the master side by about 50 [MHz]). Therefore, the interference signal of emitted s polarized light (frequency f2) influenced by $T_{11}$ and s polarized light (frequency f1') of reference light is provided at a vicinity of the frequency of 50 [MHz]. On the other hand, the interference signal of emitted s polarized light (frequency f1) influenced by $T_{12}$ and s polarized light (frequency f1') of reference light is provided at a vicinity of DC.

By utilizing the frequency difference, from interference signals outputted from the light receiving section 9, the filter circuit 101 extracts an interference signal (high frequency component) of emitted s polarized light of T11 and reference light by a band-pass filter (passing band, vicinity of 50 [MHz]), extracts the interference signal (low frequency component) of emitted s polarized light of $T_{12}$ and reference light by a low-pass filter (passing band, vicinity of DC), and outputs the respectively filtered interference signals to the calculating section 103.

Similarly, also with regard to interference signals influenced by $T_{21}$, $T_{22}$ provided by the light receiving section 10, by utilizing the frequency difference, from the interference signals outputted from the light receiving section 10, the filter circuit 102 extracts an interference signal (high frequency component) of emitted p polarized light of $T_{21}$ and reference light (p polarized light) by a band-pass filter (passing band, vicinity of 50 [MHz]), extracts an interference signal (low frequency component) of emitted p polarized light of $T_{22}$ and reference light (p polarized light) by a low-pass filter (passing band, vicinity of DC), and outputs the respectively filtered interference signals to the calculating section 103.

Further, the calculating section 103 obtains respective elements of Jones matrix from amplitudes and phases of 4 pieces of the interference signals filtered by the filter circuits 101, 102 and obtains an optical characteristic of the measuring object 1 from Jones matrix.

In this way, the detecting section 142 detects the frequency difference of light outputted from the wavelength variable light sources 122, 132, the control section 152 controls the wavelength sweep speed of the wavelength variable light source 132 based on the frequency difference detected by the detecting section 142 and therefore, the wavelength variable light source 132 on the slave side is subjected to wavelength sweep while maintaining the constant light frequency difference (|f1−f2|) relative to the wavelength variable light source 122 on the master side. Thereby, a center frequency (|f1−f2|) of the interference signals from the light receiving sections 9, 10 is not varied. Therefore, even when the wavelength sweep speed of the wavelength variable light source 122 on the master side is not constant, Jones matrix of the measuring object 1 can accurately be measured.

Further, PBS 162 of the interference section 100 multiplexes input light of p polarized light, s polarized light to be outputted to the measuring object 1 and therefore, first, second input light can be multiplexed more efficiently than those in the case of using HM. Thereby, loss of optical power can be restrained and interference light having strong optical power can be provided.

Further, LD light source 122a, 132a of the wavelength variable light sources 122, 132 output laser light by using surface emitting lasers forming oscillators by movable mirrors formed by a semiconductor micromachining technology and therefore, cost can be reduced, and wavelength sweep speed can be accelerated. Thereby, a number of times of wavelength sweep within a predetermined time period is increased, an averaging processing can be increased, and accuracy of measurement is promoted. Further, although the interferometer of the interference section 100 is much liable to be effected with an influence of disturbance (vibration), by shortening wavelength sweep time, the influence of the disturbance can be restrained, and accuracy of measurement is promoted.

Third Embodiment

Figure 7:
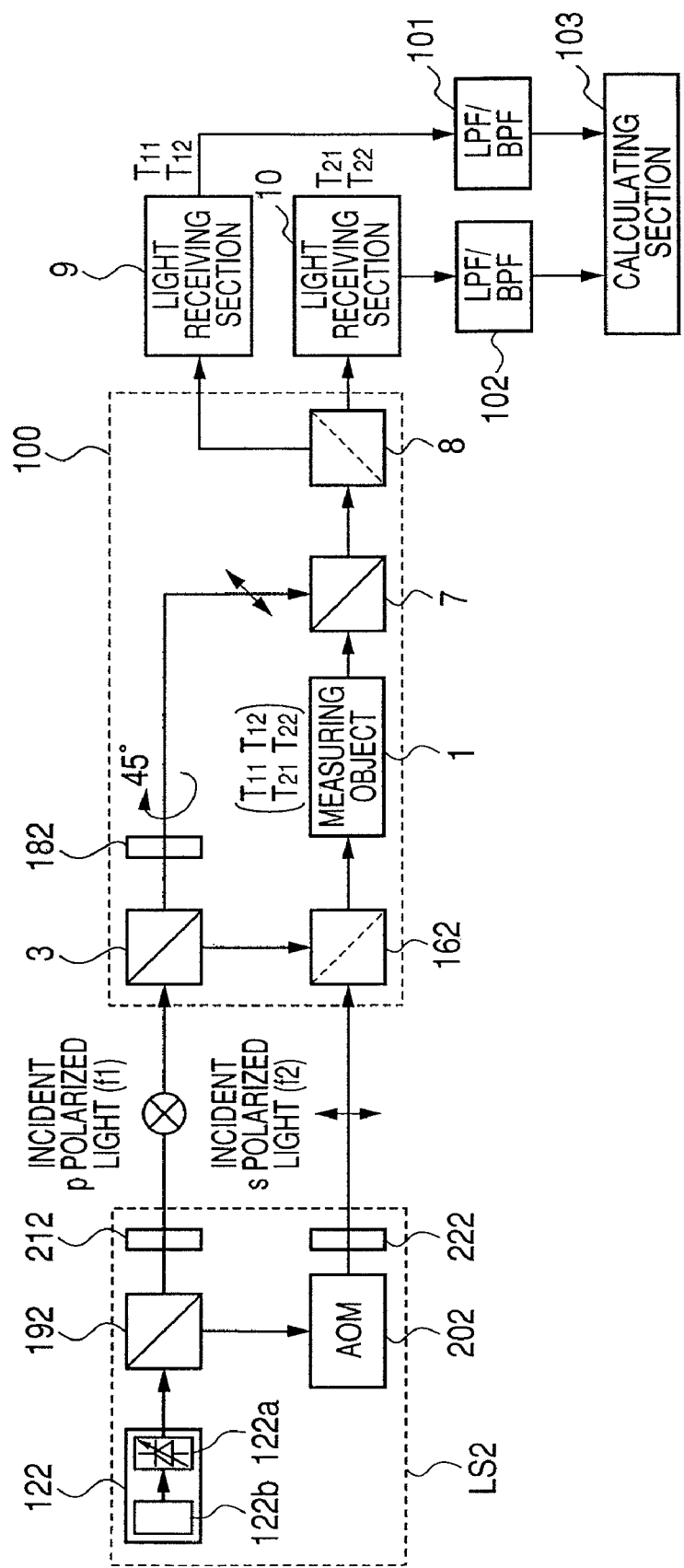
FIG. 7 is a configuration diagram showing a third embodiment of the invention.

FIG. 7 is a configuration diagram showing a third embodiment of the invention. Here, sections the same as those of FIG. 6 are attached with the same notations and an explanation thereof will be omitted. In FIG. 7, a light source section LS2 is provided in place of the light source section LS1. The light source section LS2 is provided with the wavelength variable light source 122, HM 192, an acousto-optical modulator (hereinafter, abbreviated as AOM) 202, polarized wave controllers 212, 222. Further, HM 172 of the interference section 100 is removed.

HM 192 is a branching section which branches laser light from the wavelength variable light source 122 for outputting laser light by carrying out wavelength sweep, outputs one thereof to the polarized wave controller 212, and outputs other to AOM 202. AOM 202 shifts a frequency of other branched light from HM 192 by the predetermined amount, for example, 50 [MHz].

The polarized wave controller 212 converts one branched light from HM 192 to p polarized light (first input light) to be outputted to HM 3 of the interference section 100. The polarized wave controller 222 converts light from AOM 202 to S polarized light (second input light) to be outputted to PBS 162 of the interference section 100.

Operation of the apparatus will be explained.

The wavelength sweep circuit 122b of the wavelength variable light source 122 makes the LD light source 122a output laser light similar to the apparatus shown in FIG. 6 to be subjected to wavelength sweep by a predetermined wavelength sweep speed. Further, the wavelength sweep circuit 122b reads set values (start wavelength, finish wavelength, sweep speed and the like of wavelength sweep) from a memory, not illustrated, and issues an instruction to the LD light source 122a in accordance with the set values.

Further, HM 192 branches laser light from the wavelength variable light source 122 in two, outputs one thereof to the polarized wave controller 212 and outputs other thereof to AOM 202. Further, the polarized wave controller 212 converts one branched light branched light HM 192 into p polarized light to be outputted to HM 3 of the interference section 100.

Further, AOM 202 shifts a frequency of other branched light branched by HM 192 by 50 [MHz] to be thereafter outputted to the polarized wave controller 222. Further, the polarized wave controller 222 converts the light from AOM 202 to s polarized light to be outputted to PBS 162 of the interference section 100. Therefore, incident p polarized light and incident s polarized light inputted to the interference section 100 are provided with the frequency difference of 50 [MHz]. Further, the other operation is similar to that of the apparatus shown in FIG. 6 and therefore, an explanation thereof will be omitted.

In this way, AOM 202 shifts laser light outputted from the wavelength variable light source 122 by the predetermined amount (50 [MHz]) to be outputted to the interference section 100 and therefore, light maintaining the constant light frequency difference ($|f1-f2|$) relative to the wavelength variable light source 122 is outputted. Thereby, the center frequency ($|f1-f2|$) of the interference signals from the light receiving sections 9, 10 is not varied. Therefore, even when the wavelength sweep speed of the wavelength variable light source 12 is not constant, Jones matrix of the measuring object 1 can accurately be measured.

Fourth Embodiment

Figure 8:
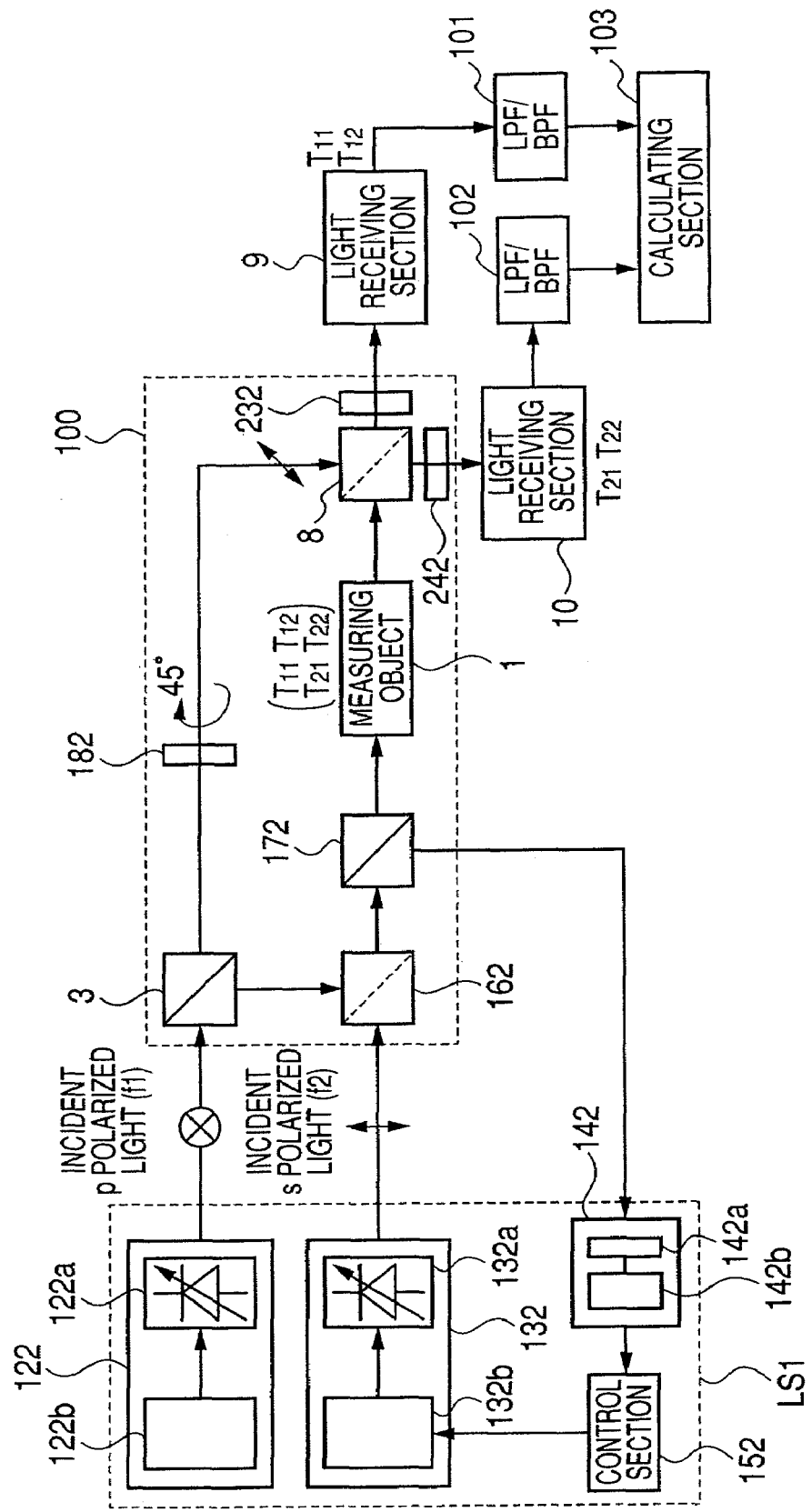
FIG. 8 is a configuration diagram showing a fourth embodiment of the invention.

FIG. 8 is a configuration diagram showing a fourth embodiment of the invention. Here, sections the same as those of FIG. 6 are attached with the same notations and an explanation thereof will be omitted. In FIG. 8, HM 7 of the interference section 100 is removed and PBS 8 multiplexes and branches reference light and signal light. Further, a polarizer 232 is provided between PBS 8 and the light receiving section 9 and a polarizer 242 is provided between PBS 8 and the light receiving section 10.

Operation of the apparatus will be explained.

PBS 8 branches output light to linearly polarized light perpendicular to each other, further, also branches reference light to linearly polarized light perpendicular to each other, multiplexes respective branched output light and reference light to be outputted to the polarizers 232, 242. Polarization planes of multiplexed light are perpendicular to each other and are not interfered with each other and therefore, the polarizers 232, 242 incline the polarization planes to be interfered with each other to be outputted to the light receiving sections 9, 10. The other operation is similar to that of the apparatus shown in FIG. 6 and therefore, an explanation thereof will be omitted.

In this way, PBS 8 carries out multiplexing and branching and therefore, in comparison of the case of using HM 7, the interference section 100 can be downsized and the optical system can be facilitated to be adjusted.

Fifth Embodiment

Although in the apparatus shown in FIG. 6 through FIG. 8, in order to obtain respective elements of $T_{11}$ through $T_{22}$ of Jones matrix, there are shown configurations of separating the low frequency components and the high frequency components from the interference signals of the light receiving sections 9, 10 by the filter circuits 101, 102, the interference section may be constituted such that all of the interference signals for obtaining the respective elements are provided by the low frequency components at vicinities of DC.

That is, output light from the measuring object 1 includes emitted s polarized light (frequencies f1, f2), emitted p polarized light (frequencies f1, f2), and the interference section is constituted to output interference light of combinations (a) through (d) shown below.

(a) p polarized light (frequency f1') of reference light and emitted p polarized light (frequencies f1, f2) of signal light.

(b) s polarized light (frequency f2') of reference light and emitted p polarized light (frequencies f1, f2) of signal light.

(c) p polarized light (frequency f1') of reference light and emitted s polarized light (frequencies f1, f2) of signal light.

(d) s polarized light (frequency f2') of reference light and emitted s polarized light (frequencies f1, f2) of signal light.

By receiving interference light of (a) through (d) described above by the light receiving section to be filtered by the low-pass filter at a rear stage, all of interference signals for obtaining the respective elements can be provided by low frequency components at vicinities of DC.

Here, similar to FIG. 6 through FIG. 8, signal light and reference light at the interference section are transmitted by the different optical paths and multiplexed and therefore, the frequencies f1', f2' of reference light are produced by the optical length difference. Therefore, when the frequencies of reference light immediately before being multiplexed with signal light are designated by notations f1', f2', the frequency difference (|f1−f2|) of first, second input light outputted by the light source section LS1 is set to be sufficiently larger than frequency difference (|f2−f2'|), (|f1−f1'|) produced by the optical length difference of signal light and reference light.

Figure 9:
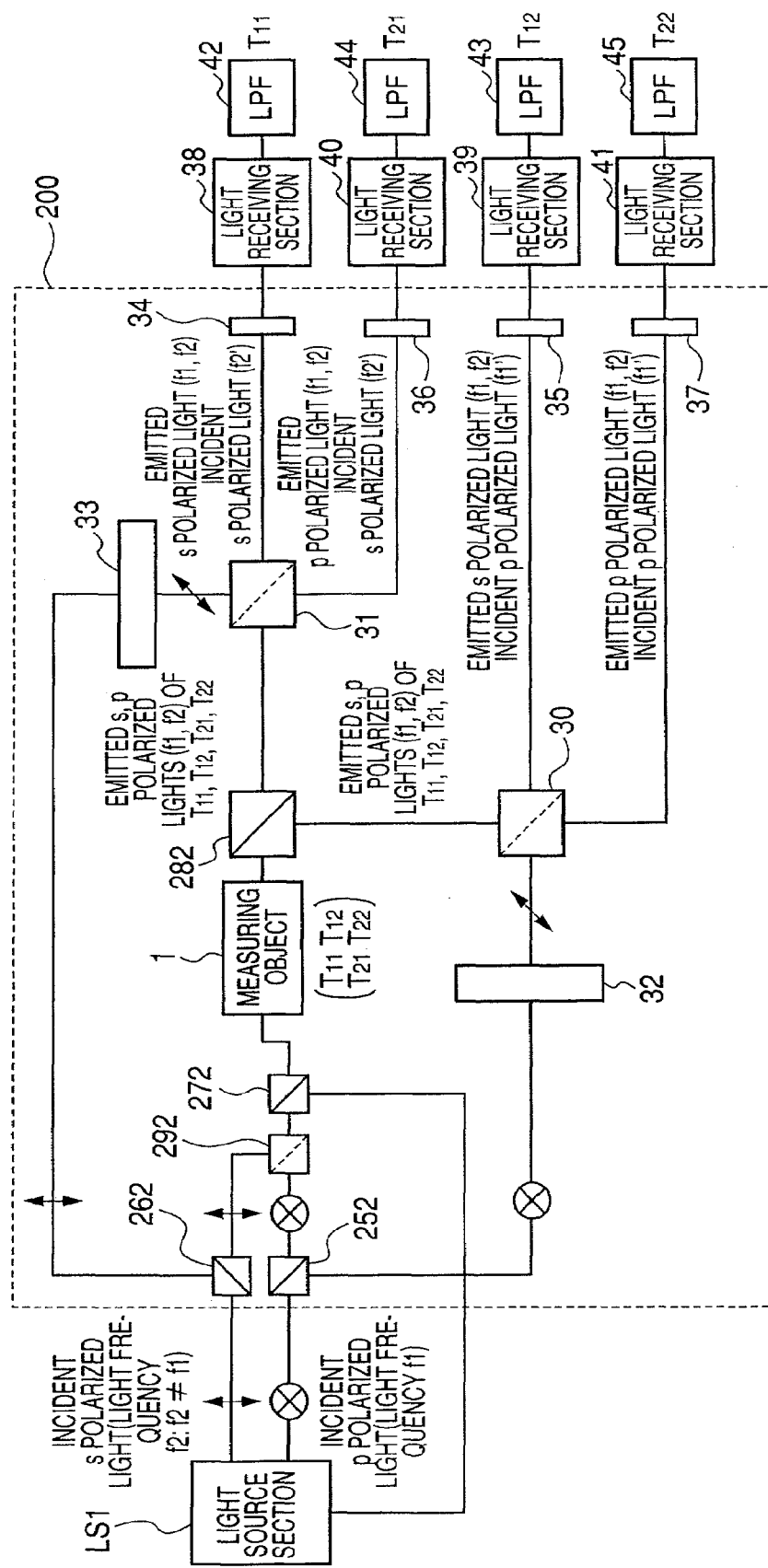
FIG. 9 is a configuration diagram showing a fifth embodiment of the invention.

FIG. 9 is a configuration diagram showing a fifth embodiment of the invention. Here, sections the same as those of FIG. 8 are attached with the same notations and an explanation thereof will be omitted. In FIG. 9, an interference section 200 is provided in place of the interference section 100.

The interference section 200 outputs interference light of (a) through (d) mentioned above. Further, multiplexed light of incident s polarized light and incident p polarized light is outputted from the light receiving section LS1.

The light receiving sections 38 through 41 are provided in place of the light receiving sections 9, 10, provided for respective interference light outputted from the interference section 200, receives interference light and outputs signals in accordance with optical power of interference light.

The low-pass filters 42 through 45 are provided in place of the filter circuits 101, 102, provided for respective the light receiving sections 38 through 41, filter signals outputted from the respective light receiving sections 38 through 41, pass only signals of frequency components lower than the frequency difference (|f1−f2|) of incident s polarized light and incident p polarized light to be outputted to the calculating section 103 (not illustrated).

Operation of the apparatus will be explained.

The light source section LS1 outputs incident p polarized light, incident s polarized light subjected to wavelength sweep continuously in predetermined wavelength ranges. Naturally, the light source section LS1 controls incident p polarized light and incident s polarized light such that a frequency difference therebetween becomes constant based on multiplexed light from the interference section 200.

The interference section 200 branches incident s polarized light, incident p polarized light and outputs one thereof to the measuring object 1 as signal light. Naturally, output light from the measuring object 1 includes emitted s polarized light and emitted p polarized light in correspondence with incident s polarized light, and emitted S polarized light and emitted p polarized light in correspondence with incident p polarized light.

Further, the interference section 200 multiplexes emitted s polarized light, emitted p polarized light from the measuring object 1 with incident s polarized light, incident p polarized light of reference light to be interfered with each other.

Specifically, interference light of emitted s polarized light (frequencies f1, f2) and incident s polarized light (f2') is outputted to the light receiving section 38, interference light of emitted s polarized light (frequencies f1, f2) and incident p polarized light (f1') is outputted to the light receiving section 39, interference light of emitted p polarized light (frequencies f1, f2) and incident s polarized light (f2') is outputted to the light receiving section 40, interference light of emitted p polarized light (frequencies f1, f2) and incident p polarized light (f1') is outputted to the light receiving section 41.

Further, the respective light receiving sections 38 through 41 output signals in accordance with optical power of interference light to the low-pass filters 42 through 45. Further, the low-pass filters 42 through 45 pass signals of low frequency components (for example, DC through about 200 [kHz]) of interference signals outputted from the light receiving sections 38 through 41 to be outputted to the calculating section 103, not illustrated, at a rear stage.

A specific explanation will be given by the light receiving section 38. The light receiving section 38 is inputted with emitted s polarized light (frequencies f1, f2), that is, signal light operated by $T_{11}$, $T_{12}$ of Jones matrix and reference light (frequency f2'). Therefore, by filtering the interference signal of the light receiving section 38 by the low-pass filter 42, as the interference signal (incident s polarized light of frequency f2', emitted s polarized light of frequency f2) after having been filtered, only the interference signal operated by only $T_{11}$ of Jones matrix is extracted.

Generally, as the interference signals after having been filtered by respective the low-pass filters 42 through 45, only the interference signals operated by only $T_{12}$, $T_{21}$, $T_{22}$ of Jones matrix are extracted.

Further, the calculating section 103 obtains the respective elements of Jones matrix from amplitudes and phases of the interference signals constituting output signals from the low-pass filters 42 through 45 and obtains an optical characteristic of the measuring object 1 from Jones matrix.

Next, details of the interference section 200 will be explained.

The interference section 200 includes branching sections 252 through 282, a multiplexing section 292, PBS 30, 31, wave plates 32, 33, polarizers 34 through 37.

Further, the branching sections 252 through 282 branch light without depending on the polarized state, and are, for example, HM, non-polarization beam splitters, optical fiber couplers or the like. Further, the wave plates 32, 33 are polarization plane rotating sections and are, for example, ½ wave plates or the like.

The first input light branching section 252 branches incident p polarized light (frequency f1) from the light source section LS1 in two, outputs one thereof to the multiplexing section 292 as signal light and outputs other thereof to the wave plate 32 as reference light.

The second input light branching section 262 branches incident s polarized light (frequency f2) from the light source section LS1 in two, outputs one thereof to the multiplexing section 292 as signal light and outputs other thereof to the wave plate 33 as reference light.

The multiplexing section 292 is, for example, PBS, a non-polarization beam splitter, HM, an optical fiber coupler or the like for multiplexing signal from the light branching sections 252, 262 to be outputted to the measuring object 1.

The branching section 272 for the light source is provided between the multiplexing section 292 and the measuring object 1 for branching multiplexed light of incident p polarized light, incident s polarized light to be outputted to the measuring object 1, the light source section LS1.

The output light branching section 282 branches output light (signal light) from the measuring object 1 in two, outputs one thereof to PBS 30 and outputs other thereof to PBS 31.

The wave plate 32 is provided between the branching section 252 and PBS 30 and inclines a polarization plane of incident p polarized light of reference light by 45°. The wave plate 33 is provided between the branching section 262 and PBS 31 and inclines a polarization plane of incident s polarized light of reference light by 45°.

The first PBS 30 multiplexes one branched light (signal light) from the branching section 282 and incident p polarized light of reference light from the wave plate 32 to be branched in two of light of polarization planes perpendicular to each other to be outputted to the polarizers 35, 37.

The second PBS 31 multiplexes other branched light (signal light) from the branching section 282 and incident s polarized light of reference light from the wave plate 33 to be branched in two of light of polarization planes perpendicular to each other to be outputted to the polarizers 34, 36.

Respective the polarizers 34 through 37 are provided for respective branched light of PBS 30, 31, that is, provided between PBS 31 and the light receiving section 38, between PBS 30 and the light receiving section 39, between PBS 31 and the light receiving section 40, between PBS 30 and the light receiving section 41.

Operation of the interference section 200 will be explained.

The branching section 252 branches incident p polarized light (frequency f1) from the light source section LS1 in two, outputs one thereof to the multiplexing section 292 as signal light and outputs other thereof to the wave plate 32 as reference light. Further, the branching section 262 branches incidents polarized light (frequency f2) from the light source section LS1 in two, outputs one thereof to the multiplexing section 292 as signal light and outputs other thereof to the wave plate 33 as reference light. Further, respective the wave plates 32, 33 incline polarization planes of reference light by 45°.

Further, the multiplexing section 292 multiplexes signal light from the branching sections 252, 262 to be outputted to the branching section 272. The branching section 272 branches multiplexed light to be outputted to the measuring object 1, the light source section LS1. Further, when the multiplexing section 292 multiplexes light by using PBS, PBS can multiplexes p polarized light, s polarized light more efficiently than an optical element (for example, HM, a non-polarization beam splitter, an optical fiber coupler or the like) for multiplexing and branching light without depending on the polarized state. Thereby, loss of optical power can be restrained and interference light having strong optical power can be provided.

Further, the branching section 282 branches output light (emitted p polarized light (frequencies f1, f2), emitted s polarized light (frequencies f1, f2)) outputted from the measuring object 1 in two, outputs one thereof to PBS 30 and outputs other thereof to PBS 31. Naturally, emitted s polarized light is operated by $T_{11}$, $T_{12}$, emitted p polarized light is operated to $T_{21}$, $T_{22}$.

Further, PBS 30 multiplexes reference light (incident p polarized light (frequency f1')) from the wave plate 32, signal light (emitted s polarized light (frequencies f1, f2), emitted p polarized light (frequencies f1, f2)) to be thereafter branched to light polarization planes of which are perpendicular to each other, outputs one thereof to the polarizers 35 and outputs other thereof the to the polarizer 37.

Thereby, one branched light of branched light outputted from PBS 30 is light multiplexed with incident p polarized light (frequency f1') and emitted s polarized light (frequencies f1, f2), and other branched light becomes light multiplexed with incident p polarized light (frequency f1') and emitted p polarized light (frequencies f1, f2).

Further, polarization planes of light multiplexed and branched by PBS 30 are perpendicular to each other and therefore, interfered with each other by inclining polarization planes by the polarizers 35, 37 to be received by the light receiving sections 39, 41.

Similarly, PBS 31 multiplexes reference light (incident S polarized light (frequency f2')) from the wave plate 33 and signal light (emitted s polarized light) frequencies f1, f2), emitted p polarized light (frequencies f1, f2)) to be thereafter branched to light polarization planes of which are perpendicular to each other, outputs one thereof to the polarizer 34 and outputs other thereof to the polarizer 36.

Thereby, one branched light of branched light outputted from PBS 31 is light multiplexed with incident s polarized light (frequency f2') and emitted s polarized light (frequencies f1, f2) and other branched light becomes light multiplexed with incident s polarized light (frequency f2') and emitted p polarized light (frequencies f1, f2).

Further, polarization planes of light multiplexed and branched by PBS 31 are perpendicular to each other and therefore, interfered with each other by inclining polarization planes by the polarizers 34, 36 to be received by the light receiving sections 38, 40.

Further, respective the low-pass filters 42 through 45 filter output signals from the light receiving sections 38 through 40 as described above, respective signals after having been filtered becomes interference signals operated by only $T_{11}$, $T_{12}$, $T_{21}$, $T_{22}$ of Jones matrix.

In this way, the interference section 200 outputs interference light of incident p polarized light and emitted S polarized light, interference light of incident p polarized light and emitted p polarized light, interference light of incident s polarized light and emitted s polarized light, interference light of incident s polarized light and emitted p polarized light and filters the interference signals by the low-pass filters 42 through 45. Thereby, the interference signals of low frequency components passing through the low-pass filters 42 through 25 can further alleviate an influence of the frequency difference of incident s polarized light and incident p polarized light produced by nonlinearity of frequency sweep of the light source section LS1. Therefore, even when the frequency difference of incident p polarized light and incident s polarized light is varied, the frequency difference can accurately be measured. Further, only the signals of the low frequency components are dealt with and therefore, a band-pass filter is not needed, circuit design of the low-pass filters 42 through 45, electric circuits or the like at a rear stage of the filters is facilitated and circuit configuration is simplified.

Further, the invention is not limited to the second to the fifth embodiments but may be as shown below.

Although in the apparatus shown in FIG. 6 through FIG. 8, there is shown a configuration of branching light by HM 3, 172, 192, any configuration will do so far as the configuration branches light without depending on the polarized state and may be, for example, a non-polarization beam splitter, an optical fiber coupler or the like.

Although in the apparatus shown in FIG. 6 through FIG. 8, there is shown a configuration of constituting reference light by branching incident p polarized light, reference light may be constituted by branching incident s polarized light, and both of incident p polarized light, incident s polarized light may be used for reference light.

In the apparatus shown in FIG. 6, FIG. 8, VCSEL 122a, 132a may be provided on the same board and may be formed by one chip.

Although in the apparatus shown in FIG. 6, FIG. 8, FIG. 9, there is shown a configuration of controlling the wavelength sweep speed of the wavelength variable light source 132 by the control section 152, a wavelength sweep speed of the wavelength variable light source 122 or both of the wavelength variable light sources 122, 132 may be controlled.

Although in the apparatus shown in FIG. 6 through FIG. 9, there is shown a configuration in which the light sources section LS1, LS2 output first, second input light by p polarized light, s polarized light which are constituted by linearly polarized light and polarization planes of which are perpendicular to each other, the polarized states of first, second input light may be perpendicular to each other, and first, second input light may be constituted by, for example, circularly polarized light, elliptically polarized light or the like.

Although in the apparatus shown in FIG. 6 through FIG. 9, there is shown a configuration of branching output light (emitted p polarized light, emitted s polarized light) for interfering with reference light respectively to linearly polarized light, output light including frequencies f1, f2 may be branched to light of a first polarized state and light of a second polarized state to be respectively interfered with reference light. Further, the first, the second polarized states are perpendicular to each other.

In the apparatus shown in FIG. 6 through FIG. 9, the interference section 100, 200 may be constituted by an interferometer of a spatial light type. By constituting the interference section 100, 200 by the interferometer of the spatial light type, an optical system can be downsized and can be made to be strong at vibration.

Although in the apparatus shown in FIG. 6 through FIG. 9, there is shown a configuration of using the interferometer of Mach-Zender type of the interference sections 100, 200, any two light flux interferometer may be used.

Although in the apparatus shown in FIG. 6 through FIG. 9, there is shown a configuration of using VCSEL for the LD light sources 122a, 132a, other wavelength variable laser may be used.

In the apparatus shown in FIG. 7, as shown by FIG. 8, HM 7 of the interference section 100 may be removed and signal light and reference light may be multiplexed and branched by PBS 8.

In the apparatus shown in FIG. 7, as shown by FIG. 9, the interference section 200 may be used in place of the interference section 100. In this case, the branching section 272 may not be provided.

Sixth Embodiment

Figure 10:
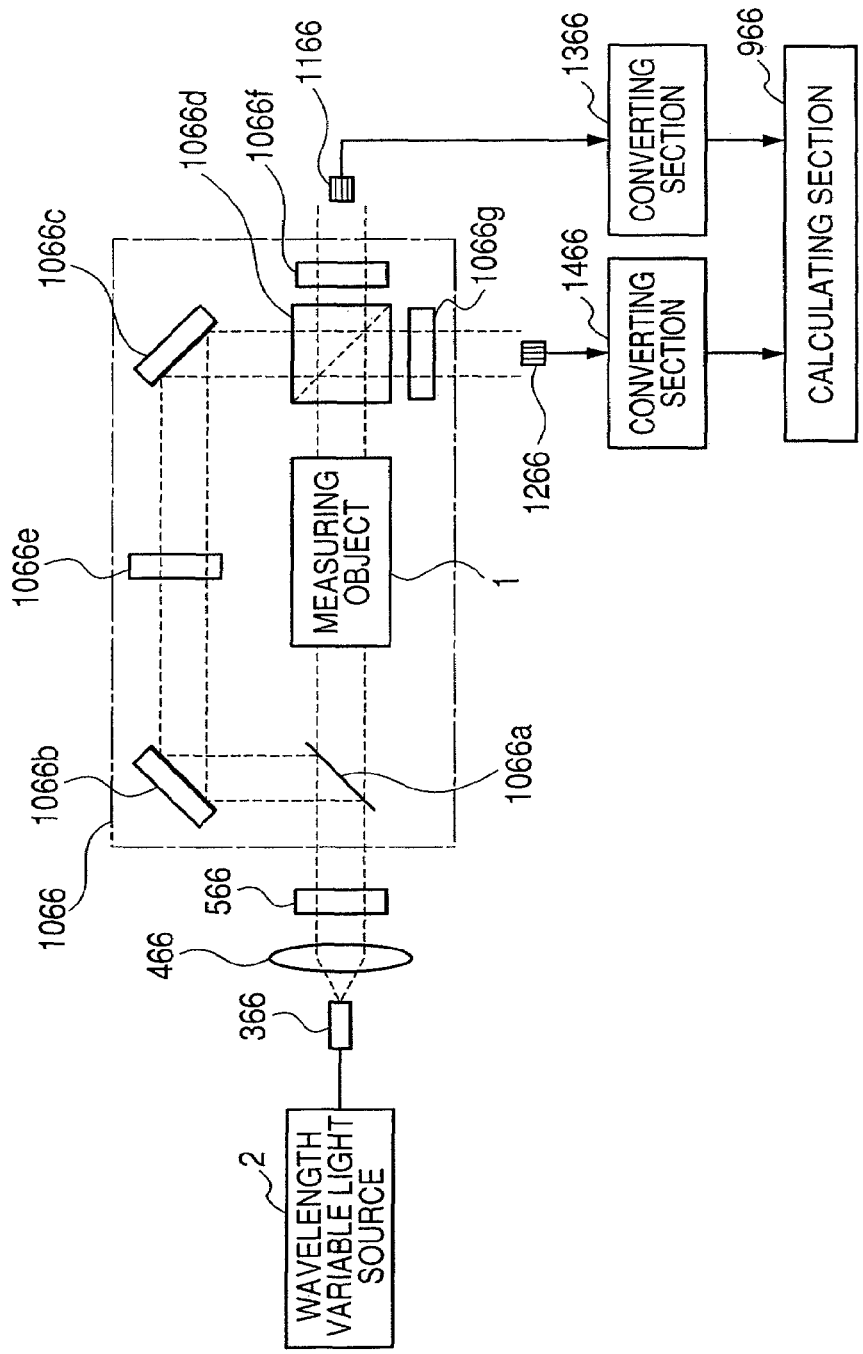
FIG. 10 is a configuration diagram showing a sixth embodiment of the invention.
Figure 11:
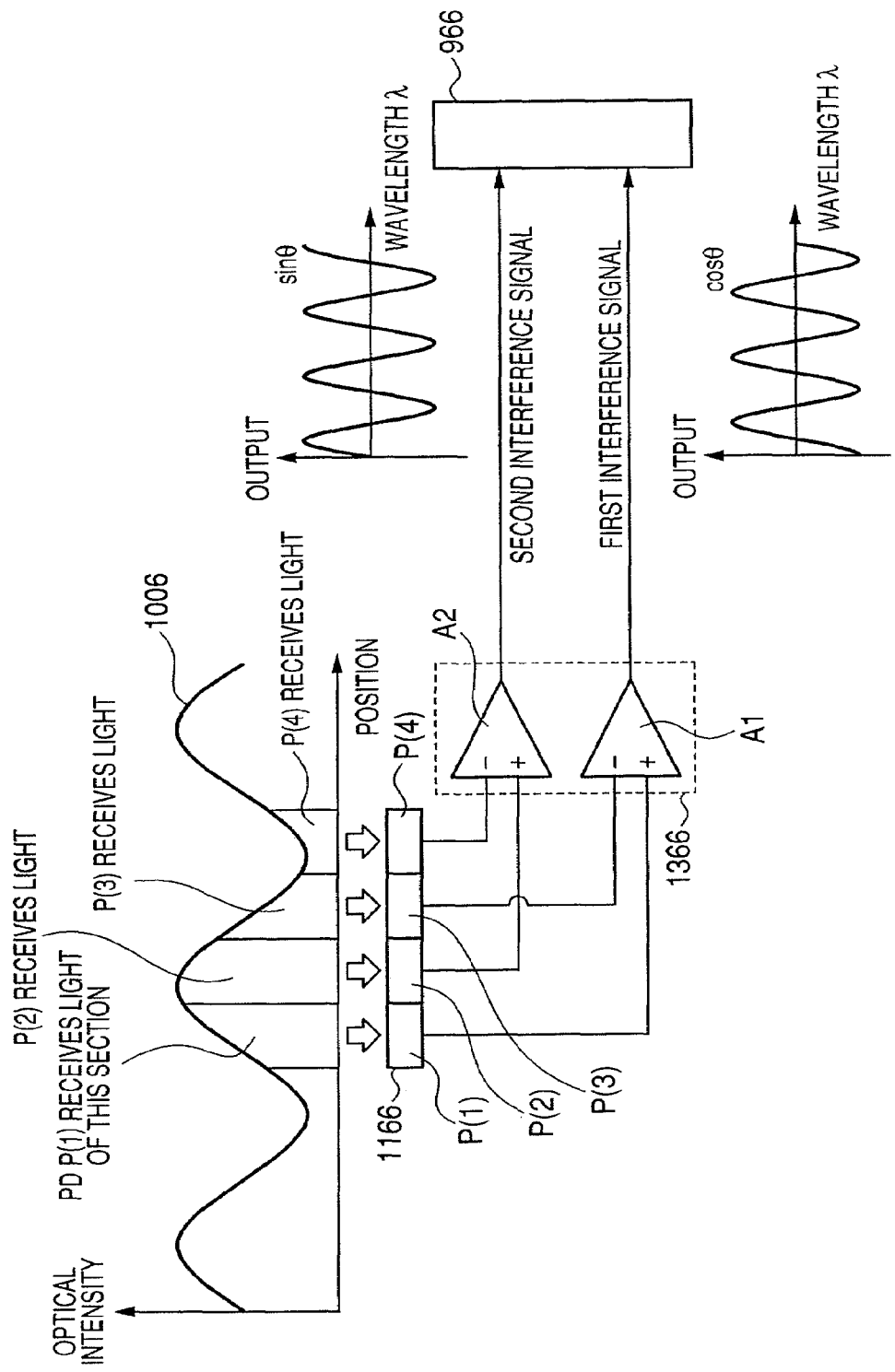
FIG. 11 is a diagram showing an essential section of the apparatus shown in FIG. 10.
Figure 17:
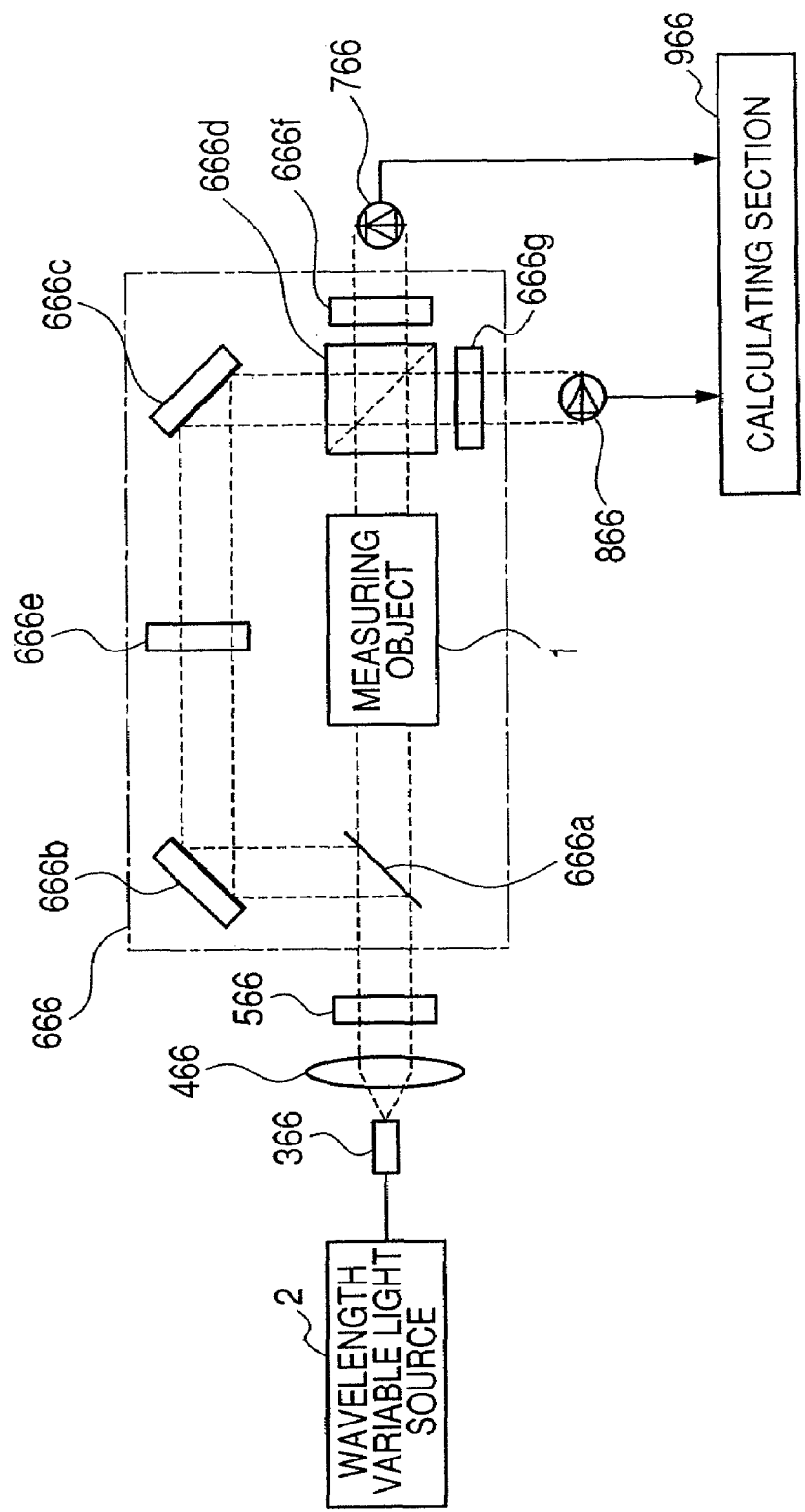
FIG. 17 is a diagram showing a configuration of optical characteristic measuring apparatus of a related art.

FIG. 10 is a configuration diagram showing a sixth embodiment of the invention. FIG. 11 is a diagram showing in details of an essential section of the apparatus shown in FIG. 10. Here, sections the same as those of FIG. 17 are attached with the same notations and an explanation thereof will be omitted. In FIG. 10, an interference section 1066 is provided in place of the interference section 666. Further, photodiode arrays 1166, 1266 are provided in place of the photodiodes 766, 866. Further, interference signal converting sections 1366, 1466 are provided between the photodiode arrays 1166, 1266 and the calculating section 966.

The interference section 1066 includes HM 1066a, mirrors 1066b, 1066c, PBS 1066d, a polarization plane rotating section 1066e, polarizers 1066f, 1066g, branches light from the polarized wave controller 566, inputs one branched light to the measuring object 1, outputs interference light by multiplexing other branched light (reference light) with output light (signal light) outputted from the measuring object 1, inclines an optical axis of output light and an optical axis of reference light to provide a predetermined angle to an optical axis angle formed by the two optical axes to be multiplexed to form spatial interference fringes.

Respective HM 1066a, the mirror 1066b, PBS 1066d, the polarization plane rotating section 1066e, the polarizers 1066f, 1066g are similar to HM 666a, the mirror 666b, PBS 666d, the polarization plane rotating section 666e, the polarizers 666f, 666g and an explanation thereof will be omitted.

The mirror 1066c is installed such that although the mirror 1066c reflects reference light reflected by the mirror 1066b and having a polarization plane inclined by the polarization plane rotating section 1066e, an optical axis of reference light after having been multiplexed and branched by PBS 1066d and an optical axis of signal light are not in parallel with each other and signal light and reference light are multiplexed while being shifted from each other by a small angle. Thereby, the interference section 1066 generates interference fringes in an optical intensity distribution in a beam face of interference light.

The photodiode arrays 1166, 1266 each includes 4 pieces of photodiodes. An explanation will be given in details in reference to FIG. 11. Both of the photodiode arrays 1166, 1266 are constructed by the same configuration and therefore, an explanation will be given by illustrating the photodiode array 1166.

The photodiode arrays 1166, 1266 each includes photodiodes P(1) through P(4). Each of the photodiodes P(1) through P(4) receives light by equally dividing one spatial period of interference fringes formed by the interference section 1066 by four. Naturally, the photodiodes P(1) through P(4) are aligned by being shifted along a direction of forming interference fringes. In other words, the photodiodes P(1) through P(4) are arranged by shifting phases thereof by 90° at the period of the interference fringes.

Here, an optical intensity distribution 1006 of the interference lights from PBS 1066d in FIG. 11 schematically shows an optical intensity of the interference fringes formed on light receiving faces of the photodiodes P(1) through P(4).

The optical intensity constitutes such interference fringes because as described above, the optical intensity distribution 1006 shown in FIG. 11 is generated in the beam face of interference light by multiplexing reflected light (reference light) from the mirror 1066c and output light (signal light) of the measuring object 1 by PBS 1066d by inclining wave faces thereof.

Further, in FIG. 11, a first, a second, a third, a fourth are constituted from the photodiode P(1) on the left side. Further, light non-receiving sections among the photodiodes P(1) through P(4) may be reduced such that light receiving sections of the photodiodes P(1) through P(4) are provided with a width constituted by equally dividing one spatial period of the interference fringes by four.

Further, the period of the interference fringes differs by a wavelength of measured light and therefore, for example, in a center wavelength in a wavelength measuring range, a width of a total of 4 pieces of the photodiodes P(1) through P(4) and the period of the interference fringes may coincide with each other.

Specifically, when an angle of inclining wave faces of signal light and reference light is increased, an interval between the interference fringes is narrowed and when the inclined angle is reduced conversely, the interval between the interference fringes is widened. Further, when the angle of inclining the wave faces is finally nullified (parallel), a uniform optical intensity is achieved. Therefore, the width is made to coincide with the period of the interference fringes by a desired wavelength by adjusting to incline the mirror 1066c in consideration of a light receiving width of the photodiodes P(1) through P(4), the interval between the interference fringes and the like.

Further, the interference fringes are moved in a transverse direction (direction of aligning the photodiodes P(1) through P(4)) by a change in a phase difference of signal light and reference light, that is, by a wavelength of laser light.

The interference signal converting sections 1366, 1466 each includes 2 pieces of subtracting circuits, generates a first, a second interference signal phases of which are shifted from each other from respective outputs of the photodiode arrays 1166, 1266 to be outputted to the calculating section 966. Both of the interference signal converting sections 1366, 1466 are constructed by the same configuration and therefore, an explanation will be given by illustrating the interference signal converting section 1366.

The interference signal converting sections 1366, 1466 each includes subtracting circuits A1, A2. The subtracting circuit A1 outputs a result of subtracting an output of the third photodiode P(3) from an output of the first photodiode P(1) to the calculating section 966 as the first interference signal. The subtracting circuit A2 outputs a result of subtracting an output of the fourth photodiode P(4) from an output of the second photodiode P(2) to the calculating section 966 as the second interference signal. Therefore, phases of the first interference signal and the second interference signal are shifted from each other and the phases are shifted from each other by 90° by a predetermined wavelength (for example, center wavelength in measured wavelength range.

Operation of the apparatus will be explained.

Wavelength sweep is carried out twice in a predetermined wavelength range in order to input respective p polarized light and s polarized light to the measuring object 1 similar to the apparatus shown in FIG. 17. First, first wavelength sweep will be explained.

First, at first wavelength sweep, similar to the apparatus shown in FIG. 17, laser light (p polarized light) of parallel light outputted from the wavelength variable light source 2 and passing through the optical fiber 366, the lens 466, the polarized wave controller 566 is inputted to the interference section 1066.

Further, HM 1066a branches light from the polarized wave controller 566, outputs one thereof to the measuring object 1 as signal light and outputs other thereof to the mirror 1066b as reference light. Further, the polarization plane rotating section 1066e inclines a polarization plane of reflected light from the mirror 1066b by 45° relative to the optical axis PBS 1066d to be outputted to the mirror 1066c such that optical power is uniformly branched at PBS 1066d at a rear stage. Further, an optical axis of reflected light to the mirror 1066c and an optical axis of output light of the measuring object 1 may be made to be in parallel with each other.

Further, an optical axis of reflected light by the mirror 1066c is not orthogonal to the optical axis of output light from the measuring object 1 but shifted therefrom slightly to be inputted to PBS 1066d. Further, PBS 1066d multiplexes output light (emitted s polarized light, emitted p polarized light in correspondence with inputted p polarized light) from the measuring object 1 and reference light by way of the mirrors 1066b, 1066c to be branched in two of light (p polarized light, S polarized light) polarization planes of which are orthogonal to each other.

Further, according to multiplexed light outputted from PBS 1066d, an optical axis angle formed by the optical axis of signal light and the optical axis of reference light is provided with a small angle. Thereby, the spatial interference fringes are formed on light receiving faces of the photodiode arrays 1166, 1266. Naturally, output light from the measuring object 1 is signal light. Further, both of signal light and reference light to be multiplexed may be constituted by parallel light.

Further, polarization planes of light (signal light and reference light) multiplexed and branched by PBS 1066d are orthogonal to each other, the polarization planes are inclined by the polarizers 1066f, 1066g to be interfered with each other to be received by the photodiode arrays 1166, 1266.

Further, the photodiode array 1166 is inputted with interference light of signal light operated by $T_{22}$ of Jones matrix and reference light. Further, the photodiode array 1266 is inputted with interference light of signal light operated by $T_{12}$ of Jones matrix and reference light.

The respective photodiodes P(1) through P(4) of the photodiode arrays 1166, 1266 receive multiplexed interference light from PBS 1066d and output electric signals in accordance with optical power of received interference light to the interference signal converting sections 1366, 1466.

Further, the subtracting circuits A1 of the interference signal converting sections 1366, 1466 calculates (output of first photodiode P (1))–(output of third photodiode P (3)) and outputs a result of subtraction to the calculating section 966 as first interference signals.

Further, the subtracting circuits A2 of the interference signal converting sections 1366, 1466 calculate (output of second photodiode P(2))–(output of fourth photodiode P(4)) and outputs a result of subtraction to the calculating section 966 as second interference signals. Naturally, also amounts of offset of both of the first and the second interference signals are removed.

The calculating section 966 calculates a moving direction and an moving amount the interference fringes from the first and the second interference signals phases of which are shifted from each other by 90°. That is, because the moving direction and the moving amount correspond to an increase or a decrease of the phase difference of multiplexed light.

Successively, second wavelength sweep is carried out and a point of the second wavelength sweep which differs from the first wavelength sweep resides in that the polarized wave controller 566 converts laser light into s polarized light, that the photodiode array 1166 is inputted with interference light of signal light operated by $T_{21}$ of Jones matrix and reference light, that the photodiode array 1266 is inputted with interference light signal light operated by $T_{11}$ of Jones matrix and reference light, and the other operation is similar to the first wavelength sweep and therefore, an explanation thereof will be omitted.

Further, the calculating section 966 calculates respective elements of Jones matrix from phases and amplitudes of the interference signals based on respective p polarized light, s polarized light and calculates an optical characteristic of the measuring object 1 from calculated Jones matrix.

In this way, the interference section 1066 forms the spatial interference fringes by shifting the optical axis of signal light and the optical axis of the reference light from each other to be interfered with each other. Further, interference light is received by four pieces of the photodiodes P(1) through P(4) phases of which are shifted from each other by 90° relative to the period of the interference fringes. Further, the interference signal converting sections 1366, 1466 generate the first and the second interference signals phases of which are shifted from each other by 90° from the signal of the photodiode array 1166. The calculating section 966 calculates the moving direction and the moving amount the interference fringes from the first and the second interference signals and therefore, an amount of a phase including an increase or a decrease in the phase difference of multiplexed light is calculated. Thereby, an increase or a decrease in the phase difference of light (signal light and reference light) to be multiplexed can easily be determined. Therefore, the optical path length of the measuring object is not limited.

Seventh Embodiment

Figure 12:
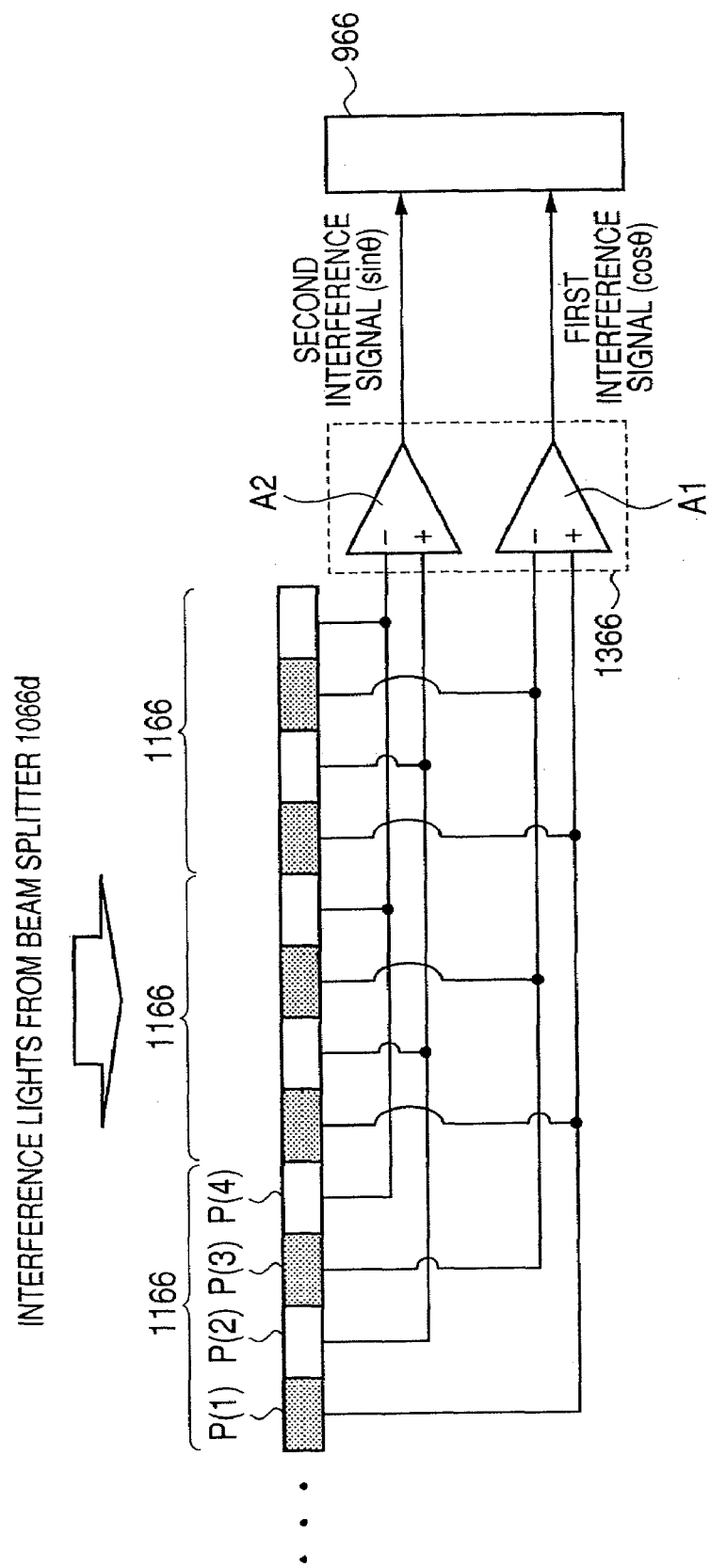
FIG. 12 is a configuration diagram showing a seventh embodiment of the invention.

FIG. 12 is a configuration diagram showing a seventh embodiment of the invention. Here, sections the same as those of FIG. 10, FIG. 11 are attached with the same notations and an explanation thereof will be omitted. In FIG. 12, pluralities of pieces of the photodiode arrays 1166, 1266 are provided along a direction of forming the interference fringes from the interference section 1066. Further, in FIG. 12, only the photodiode array 1166 is illustrated and an explanation will be given of the side of the photodiode array 1166.

Outputs of first ones of the photodiodes P(1) and outputs of third ones of the photodiodes P(3) of the respective photodiodes arrays 1166 are inputted to the subtracting circuit A1 to be subjected to subtraction and outputted as the first interference signals.

Further, outputs of second ones of the photodiodes P(2) and outputs of fourth ones of the photodiodes P(4) of the respective photodiodes arrays 1166 are inputted to the subtracting circuit A2 to be subjected to subtraction and outputted as the second interference signals. That is, the photodiodes P(1) through P(4) are wired at every 4 pieces thereof.

In this way, pluralities of pieces of respective the photodiode arrays 1166, 1266 are provided along a direction of aligning the interference fringes, and the interference signal converting sections 1366, 1466 generate the interference signals from the outputs of the pluralities of photodiode arrays 1166, 1266. Thereby, even when there is a nonuniformity (random noise) at a section or a total of the interference fringes, the interference signal which is less influenced by the nonuniformity can be provided by averaging.

Eighth Embodiment

Although according to the optical characteristic measuring apparatus shown in FIG. 10, FIG. 12, at a predetermined wavelength, the spatial period of the interference fringes and the period of the photodiode arrays 1166, 1266 coincide with each other, the more remote from the predetermined wavelength, the more shifts the period.

Figure 13:
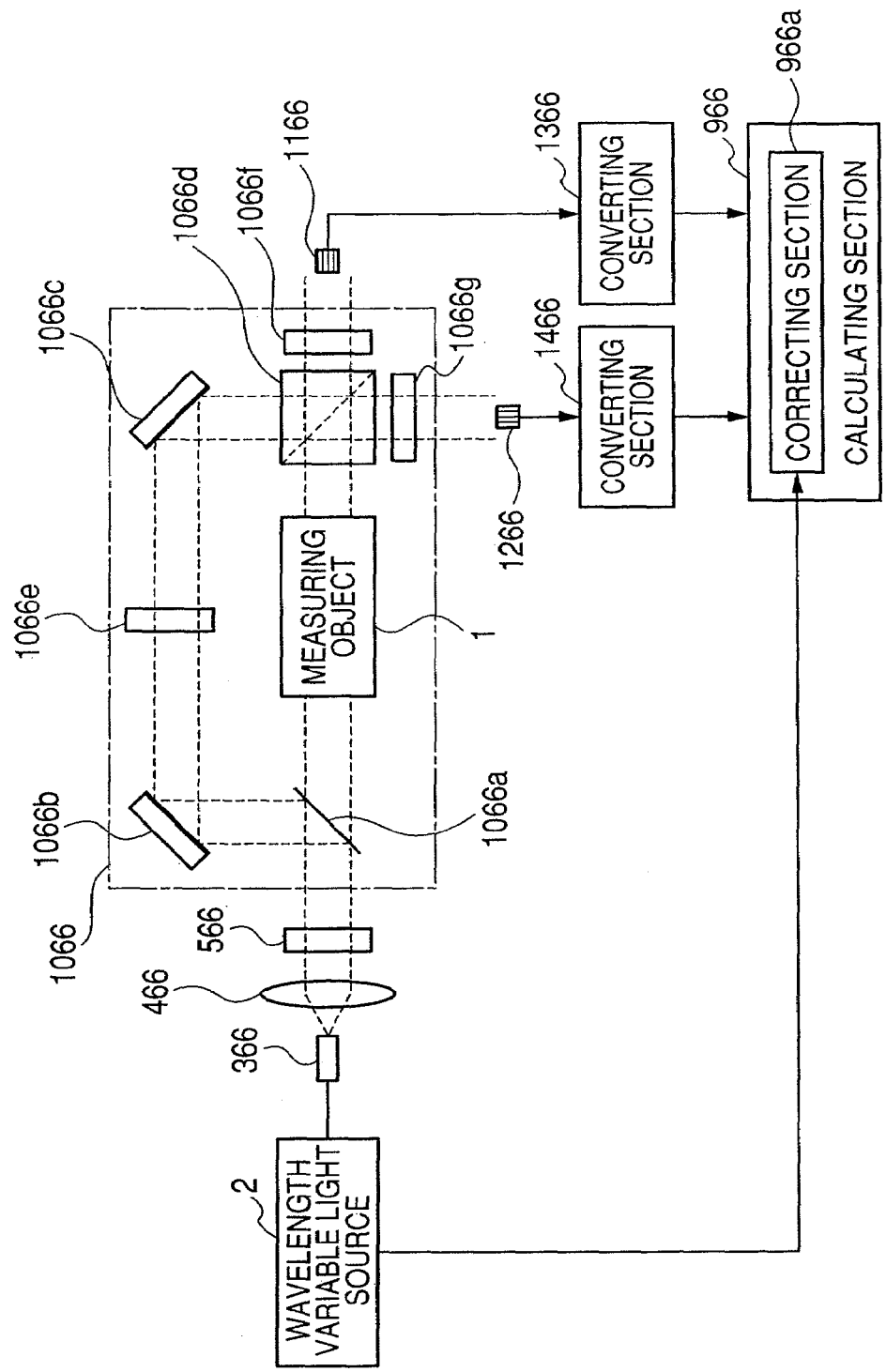
FIG. 13 is a configuration diagram showing a eighth embodiment of the invention.

FIG. 13 is a configuration diagram showing an eighth embodiment of the invention, which can calculate a moving amount the interference fringes, that is, the phase difference of multiplexed light with high accuracy. Here, sections the same as those of FIG. 10 are attached with the same notations and an explanation thereof will be omitted. In FIG. 13, the calculating section 966 is provided with correcting section 966*a*.

The correcting section 966*a* is inputted with the wavelength of laser light which is being outputted from the wavelength variable light source 2 and corrects an error in the moving amount the interference fringes by the shift between the spatial period of the interference fringes and the period of the photodiodes P(1) through P(4) of the photodiode arrays 1166, 1266.

Operation of the apparatus will be explained.

The correcting section 966*a* is inputted with the wavelength of laser light which is being outputted (for example, may be with a rough accuracy not by [pm] unit but by [nm] unit) from the wavelength variable light source 2. Further, the correcting section 966*a* calculates the shift between the spatial period of the interference fringes and the period of the photodiodes P (1) through P (4) of the photodiode arrays 1166, 1266 from the wavelength of the rough accuracy.

That is, the interference fringes are moved by depending on the wavelength of the laser light outputted from the wavelength variable light source 2. However, the period of the interference fringes is changed by the wavelength.

Therefore, the correcting section 966*a* calculates the moving amount the interference fringes relative to an amount of a change in the wavelength by calculation in consideration of a change in the period. Or, the shift between the periods depending on the wavelength is previously measured or calculated to be stored to a memory (not illustrated). Further, the correcting section 966*a* calculates the moving amount by the phase difference of multiplexed light by removing an influence of a change in the period of the interference fringes produced by the wavelength sweep.

That is, the shift in the period is uniquely determined by the wavelength and therefore, the correcting section 966*a* calculates the shift in the period by calculation or data stored to the memory.

Further, the correcting section 966*a* corrects an amount of error of the moving amount produced by the shift between the periods. Further, the calculating section 966 calculates Jones matrix of the measuring object 1 from phases and amplitudes of the interference signals based on the corrected moving amount. Other operation is similar that of the apparatus shown in FIG. 10 and therefore, an explanation thereof will be omitted.

In this way, the correcting section 966*a* corrects the error in the moving amount produced by the shift between the periods from the wavelength with rough accuracy and therefore, an increase or a decrease in the phase difference can accurately be calculated.

Further, the invention is not limited to the sixth to the eighth embodiments but may be as shown below.

Although in the apparatus shown in FIG. 10 and FIG. 13, there is shown a configuration of providing an interferometer of Mach-Zender type of the interference section 10660, any two light flux interferometer may be used, for example, a Michelson type interferometer will do. In sum, any interferometer will do so far as the interferometer generates interference fringes in a linear shape by multiplexing signal light and reference light in a state of inclining wave faces thereof.

Although in the apparatus shown in FIG. 10 and FIG. 13, there is shown a configuration of using HM 1066*a*, any element will do so far as element branches light without depending on a polarized state, for example, a non-polarization beam splitter, an optical fiber coupler or the like will do.

Although in the apparatus shown in FIG. 10, FIG. 13, there is shown a configuration of inclining the mirror 1066*c*, the optical axis of reference light and the optical axis of signal light multiplexed by PBS 1066*d* may be adjusted to a slightly inclined state and as a method of producing inclination of the two optical axes, the mirrors 1066*b*, 1066*c* may be inclined, or HM 1066*a*, PBS 1066*d* may be inclined.

Although in the apparatus shown in FIG. 10, FIG. 13, there is shown a configuration of providing the polarized wave controller 566 between the lens 466 and the interference section 1066, the polarized wave controller 566 may be provided at inside of the wavelength variable light source 2.

Although in the apparatus shown in FIG. 10, FIG. 13, there is shown a configuration of carrying out twice wavelength sweep (for outputting p polarized at first time and outputting s polarized light at second time) by the wavelength variable light source 2, the respective elements of Jones matrix may be calculated by one time wavelength sweep.

For example, the light source section outputs first, second input light frequencies of which differ from each other and polarized states of which are orthogonal to each other to the interference section 1066. Here, the first input light is constituted by p polarized light (frequency f1($t$)), and the second input light is constituted by s polarized light (frequency f2($t$), however, f1($t$)≠f2($t$)). Further, the light source section 2 carries wavelength sweep (frequency sweep) by making a frequency difference (|f1($t$)−f2($t$)|) substantially constant to be outputted to the interference section 1066. On the other hand, in signals from the photodiode arrays 1166, 1266, there are present interference signals of emitted p polarized light, emitted s polarized light and reference light respectively in correspondence with incident p polarized light, incident s polarized light. However, frequencies of incident p polarized light, incident s polarized light differ from each other and therefore, a difference in beat frequencies of the interference signals produced by the frequency difference may be filtered to separate the interference signal of s polarized light and reference light, the interference signal of p polarized light and reference light.

Further, two pieces of wavelength variable light sources may be prepared for the light source section for outputting the first, the second input light. Further, the frequency difference may be produced by branching light of one piece of the wavelength variable light source in two and delaying one light, or the frequency difference may be produced by shifting the frequency of one light (for example, by using acousto-optical modulator).

Although in the apparatus shown in FIG. 11, there is shown a configuration in which the photodiode arrays 1166, 1266 each includes 4 pieces of the photodiodes P(1) through P(4), any number of pieces thereof will do, for example, the photodiode arrays 1166, 1266 each may include at least (4×n) pieces of the photodiodes, and respective the photodiodes may receive light by equally dividing one spatial period of the interference fringes by four (that is, by installing the respective by shifting the phases by 90° relative to the period of the interference fringes).

Further, the interference signal converting sections 1366, 1466 each may output a result of subtracting an output of the (4×(i−1)+3)-th photodiode from an output of the (4×(i−1)+1)-th photodiode as the first interference signal and may output a result of subtracting an output of the (4×(i−1)+4)-th photodiode from an output of the (4×(i−1)+2)-th photodiode as the second interference signal. Incidentally, notations n, i designate natural numbers.

That is, the interference signal converting sections 1366, 1466 each outputs a result of subtracting the output of (3, 7, 11, . . . )-th photodiode from the output of (1, 5, 9, . . . )-th photodiode as the first interference signals and outputs a result of subtracting the output of (4, 8, 12, . . . )-th photodiode from the output of (2, 6, 10, . . . )-th photodiode as the second interference signals.

In this way, the photodiode arrays 1166, 1266 measure a plurality of periods of the interference fringes, and the interference signal converting sections 1366, 1466 generate the interference signals from the outputs of the photodiode arrays 1166, 1266. Thereby, even when a nonuniformity (random noise) is present at a section or a total of the interference fringes, the interference signal which is less influenced by the nonuniformity can be provided by averaging.

Although in the apparatus shown in FIG. 12, there is shown a configuration of aligning the photodiode array 1166 without a gap therebetween, a gap may be provided between the photodiode arrays 11.

Although in the apparatus shown in FIG. 13, there is a shown a configuration of inputting the wavelength which is being outputted from the wavelength variable light source 2 to the calculating section 966, when the correcting section 966$a$ is provided with start wavelength, sweep speed in carrying out wavelength sweep, an error by a shift in the period may be corrected by start wavelength, sweep speed.

It will be apparent to those skilled in the art that various modifications and variations can be made to the described preferred embodiments of the present invention without departing from the spirit or scope of the invention.

Thus, it is intended that the present invention cover all modifications and variations of this invention consistent with the scope of the appended claims and their equivalents.

What is claimed is:

1. An optical characteristic measuring apparatus for measuring an optical characteristic of a measuring object, the optical characteristic measuring apparatus comprising:
   a first wavelength variable light source which sweeps a wavelength of a first input light and outputs the first input light to an interference section;
   a second wavelength variable light source which sweeps a wavelength of a second input light and outputs the second input light to the interference section, frequencies of the first input light and the second input light being different from each other and polarized states of the first input light and the second input light being perpendicular to each other;
   the interference section which multiplexes and inputs the first input light and the second input light to the measuring object, makes output light from the measuring object interfere with at least one of the first input light and the second input light, and outputs a plurality of interference lights;
   a detecting section for detecting a frequency difference of the first input light and the second input light from the first wavelength variable light source and the second wavelength variable light source; and
   a control section for controlling a frequency difference of the first wavelength variable light source and the second wavelength variable light source based on the frequency difference detected by the detecting section.

2. The optical characteristic measuring apparatus according to claim 1, wherein at least one of the first wavelength variable light source and the second wavelength variable light source includes a surface emitting laser forming a resonator by a movable mirror being formed by a semiconductor micro-machining technology.

3. The optical characteristic measuring apparatus according to claim 1, wherein at least one of the first wavelength variable light source and the second wavelength variable light source includes a surface emitting laser forming a resonator by a movable mirror being formed by a semiconductor micro-machining technology, and
   the first wavelength variable light source and the second wavelength variable light source are provided on a same substrate.

4. The optical characteristic measuring apparatus according to claim 1, wherein the interference section includes a polarization beam splitter which multiplexes the first input light and the second input light and outputs a multiplexed light to the measuring object.

5. The optical characteristic measuring apparatus according to claim 1, wherein the interference section includes:
   a polarization beam splitter which multiplexes at least one of the first input light and the second input light with the output light from the measuring object, and branches a multiplexed light into s polarized light and p polarized light; and
   a polarization plane rotating section which inclines at least one polarization plane of the first input light and the second input light by 45°, and outputs an inclined light to the polarization beam splitter.

6. The optical characteristic measuring apparatus according to claim 1, further comprising:
   a plurality of light receiving sections which are respectively provided for the interference lights outputted from the interference section, receives the interference lights respectively, and outputs signals in accordance with optical powers of the interference lights respectively; and
   a low-pass filter for filtering the signals outputted from the light receiving sections,
   wherein the interference section branches each of the first input light and the second input light, inputs one branched light to the measuring object, makes the output light from the measuring object interfere with other branched light, and outputs the plurality of interference lights,
   the plurality of interference lights includes:
   a first interference light in which the first input light interferes with an output light in a first polarized state of the output light from the measuring object;
   a second interference light in which the second input light interferes with the output light in the first polarized state of the output light from the measuring object;
   a third interference light in which the first input light interfere with an output light in a second polarized state of the output light from the measuring object; and
   a fourth interference light in which the second input light interferes with the output light in the second polarized state of the output light from the measuring object, and
   the first polarized state of the output light and the second polarized state of the output light are perpendicular to each other.

7. The optical characteristic measuring apparatus according to claim 6, wherein the low-pass filter passes a signal having a frequency lower than a difference of the frequencies of the first input light and the second input light.

8. The optical characteristic measuring apparatus according to claim 1, wherein the interference section is an interferometer of a spatial light type.

* * * * *